United States Patent
Hanold et al.

(10) Patent No.: US 11,776,668 B2
(45) Date of Patent: Oct. 3, 2023

(54) CAPTURING PERSON-SPECIFIC SELF-REPORTED SUBJECTIVE EXPERIENCES AS BEHAVIORAL PREDICTORS

(71) Applicant: ADoH Scientific, LLC, Mount Pleasant, SC (US)

(72) Inventors: Gregg T. Hanold, Charleston, SC (US); Brian Sullivan, Charleston, SC (US); Corley Sullivan, Charleston, SC (US)

(73) Assignee: ADOH SCIENTIFIC, LLC, Mount Pleasant, SC (US)

( * ) Notice: Subject to any disclaimer, the term of this patent is extended or adjusted under 35 U.S.C. 154(b) by 269 days.

(21) Appl. No.: 17/011,240

(22) Filed: Sep. 3, 2020

(65) Prior Publication Data

US 2021/0065854 A1    Mar. 4, 2021

Related U.S. Application Data

(60) Provisional application No. 63/068,429, filed on Aug. 21, 2020, provisional application No. 62/895,567, filed on Sep. 4, 2019.

(51) Int. Cl.
*G16H 10/20*    (2018.01)
*G16H 50/70*    (2018.01)
(Continued)

(52) U.S. Cl.
CPC ......... *G16H 10/20* (2018.01); *A61B 5/14532* (2013.01); *A61B 5/165* (2013.01);
(Continued)

(58) Field of Classification Search
CPC ........ G16H 10/20; G16H 20/30; G16H 40/20; G16H 10/60; G16H 15/00; G16H 50/30;
(Continued)

(56) References Cited

U.S. PATENT DOCUMENTS 7,720,784 B1    5/2010    Froloff
9,959,011 B2    5/2018    Sullivan et al.
(Continued)

OTHER PUBLICATIONS

PCT International Search Report for PCT International Application No. PCT/US 20/49320; Completion date: Oct. 27, 2020; dated Dec. 4, 2020.
(Continued)

*Primary Examiner* — Michael Tomaszewski
(74) *Attorney, Agent, or Firm* — Dority & Manning, P.A.

(57) ABSTRACT

Disclosed methodologies provide improved predictors of patient treatment adherence by using person-specific subjective experience and social-environmental factors. Methodologies combine emotion and data sciences. Advanced tools capture, measure, store, and analyze self-report of subjective experiences using digital applications and platforms. Patient-specific data is obtained regarding emotional or affective determinants and social determinants for generating a calculated composite score of the patient's probability of adherence or achievement relative to target outcomes, e.g. adherence to treatment plans, wellness activities, etc. for a subject individual. Internal/subjective factors are judged by self-report measures designed to validly judge tested factors based on a patient adjusting continuously-variable graphical interfaces to capture and measure subjective experiences. Emotional characteristics may include perception and intensity in each category of sickness versus wellness, stress, depression, anxiety, pain, and feelings about most recent health provider/staff interaction (with determined intensity for choices of Delighted, Satisfied, Meh, Disappointed, Frustrated). Emotional characteristics may be considered among health, and social characteristics in measuring potential obstacles to adherence.

59 Claims, 29 Drawing Sheets

(51) Int. Cl.

| | |
|---|---|
| *G16H 15/00* | (2018.01) |
| *G16H 50/30* | (2018.01) |
| *G16H 20/10* | (2018.01) |
| *G16H 20/30* | (2018.01) |
| *G06Q 30/0203* | (2023.01) |
| *G06Q 30/0282* | (2023.01) |
| *G16H 40/20* | (2018.01) |
| *G06N 20/00* | (2019.01) |
| *G06F 3/0482* | (2013.01) |
| *A61B 5/16* | (2006.01) |
| *A61B 5/145* | (2006.01) |
| *A61B 5/00* | (2006.01) |
| *G16H 10/60* | (2018.01) |
| *G06F 3/04847* | (2022.01) |

(52) U.S. Cl.
CPC .......... *A61B 5/4833* (2013.01); *A61B 5/7275* (2013.01); *A61B 5/7405* (2013.01); *A61B 5/748* (2013.01); *G06F 3/0482* (2013.01); *G06N 20/00* (2019.01); *G06Q 30/0203* (2013.01); *G06Q 30/0282* (2013.01); *G16H 10/60* (2018.01); *G16H 15/00* (2018.01); *G16H 20/10* (2018.01); *G16H 20/30* (2018.01); *G16H 40/20* (2018.01); *G16H 50/30* (2018.01); *G16H 50/70* (2018.01); *G06F 3/04847* (2013.01)

(58) Field of Classification Search
CPC ........ G16H 50/70; G16H 20/10; G06N 20/00; A61B 5/14532; A61B 5/165; A61B 5/4833; A61B 5/7275; A61B 5/7405; A61B 5/748; G06F 3/0482; G06F 3/04847; G06Q 30/0203; G06Q 30/0282
USPC ........................................................ 705/2–3
See application file for complete search history.

(56) References Cited

U.S. PATENT DOCUMENTS

| | | | |
|---|---|---|---|
| 2001/0029322 A1 | 10/2001 | Iliff | |
| 2008/0109252 A1* | 5/2008 | LaFountain | G16H 10/20 705/2 |
| 2008/0201174 A1* | 8/2008 | Ramasubramanian | G16H 20/10 705/3 |
| 2010/0205008 A1* | 8/2010 | Hua | G06Q 50/22 709/217 |
| 2012/0130196 A1* | 5/2012 | Jain | A61B 5/00 600/300 |
| 2012/0303388 A1 | 11/2012 | Vishnubhatla et al. | |
| 2015/0356701 A1* | 12/2015 | Gandy | G06Q 10/109 705/2 |

OTHER PUBLICATIONS

PCT Written Opinion of the International Searching Authority for PCT International Application No. PCT/US 20/49320; Completion date: Oct. 27, 2020; dated Dec. 4, 2020.

* cited by examiner

Interactions Among Emotional Health and Social Characteristics

7. Do you have any of the following conditions? *
   ○ Type I diabetes
   ○ Type II diabetes
   ○ Metabolic syndrome
   ○ Pre-diabetes
   ○ None of these 8. Do you have high blood pressure (hypertension)? *
   ○ Yes
   ○ No 9. Do you have any type of chronic pain? *
   ○ Yes
   ○ No

FIG. 3A

10. Do you have any other chronic medical or health conditions? *
○ Yes
○ No
11. Are you currently engaged in any form of counseling, psychotherapy, or other services (aside from medications) to help with depression, anxiety, stress, or chronic pain? *
○ Yes
○ No
FIG. 3B

14. In the area where you live would you say the average household uses one or more of the following social programs: WIC, Food Stamps, Meals on Wheels, food kitchens? *

○ Yes

○ No

15. In the area where you live *

○ Most households rent their home

○ Most households own their home

FIG. 4B

16. In the area where you live, please indicate which level you believe the average yearly household income to be *

○ less than $20,000

○ $20,000 - $60,000

○ $60,001 - $120,000

○ $120,001 - $250,000

○ greater than $250,000

17. In the area where you live would you say that there are households living at or below the poverty level (less than $20,000 annual income)? *

○ Yes

18. In the area where you live would you say the average household spends more than 30% of their annual income on housing? *

○ Yes
○ No

19. Regarding the area where you live, please select one of the following *

○ The children in most families complete high school only
○ The children in most families enroll in college 20. In the area where you live would you say that English is the primary language in most households? *

○ Yes
○ No

FIG. 4D

21. In the area where you live, would you say most households vote in elections? *

○ Yes
○ No

22. In the area where you live would you say the ethnic diversity is *

○ High
○ Medium
○ Low

23. In the area where you live, how many people (on average) would you say live in each household? *

○ 1
○ 2
○ 3
○ 4
○ 5 or more

FIG. 4E

24. In the area where you live would you say most people have health insurance? *

○ Yes

○ No

25. In the area where you live would you say most people *

○ Have a specific primary care doctor

○ use mainly emergency rooms, urgent care facilities, or free clinics

26. In the area where you live would you say most people have access to a physician who speaks their native language? *

○ Yes

27. In the area where you live, for groceries, would you say that people mainly rely on *

○ Convenience stores (e.g. 7-11, circle K, gas marts)

○ Variety stores (e.g. Dollar General, Family Dollar, Dollar Tree)

○ Superstores (e.g. Costco, Walmart, Sam's Club)

○ Grocery stores (e.g. Harris Teeter, Kroger, Safeway, Albertsons)

28. In the area where you live, would you say crime and violence are *

○ High
○ Medium
○ Low

29. In the area where you live would you say most home residences have working air conditioning/heat? *

○ Yes
○ No

FIG. 4G

30. In the area where you live, what would you say is the average age of the homes? *

○ Built less than 10 years ago
○ Built less than 15 years ago
○ Built less than 20 years ago
○ Built less than 50 years ago
○ Built more than 50 years ago

| LTA Score | Risk of non-adherence |
|---|---|
| 0.0 - 33.3 | High |
| 33.4 - 66.6 | Moderate |
| 66.7 - 100.0 | Low |

FIG. 5C

PAIR High-Level Architecture

|  | Correlation (r) with number of behaviors | |
|---|---|---|
|  | Positive | Negative |
| Love | .35 | .04 |
| Delighted | .25 | -.05 |
| Satisfied | .03 | -.17 |
| Meh | -.24 | -.16 |
| Disappointed | -.11 | .05 |
| Frustrated | -.15 | .10 |
| Hate | -.19 | .25 |

FIG. 11

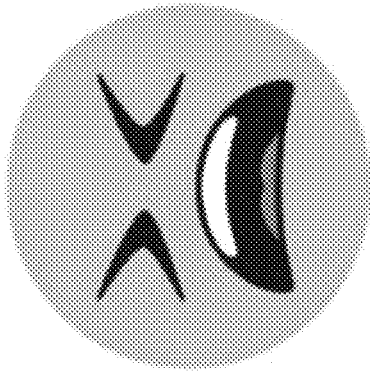
FIG. 15A

CAPTURING PERSON-SPECIFIC SELF-REPORTED SUBJECTIVE EXPERIENCES AS BEHAVIORAL PREDICTORS

PRIORITY CLAIMS

This application claims the benefit of previously filed U.S. Provisional Patent Application entitled "PERSON-SPECIFIC SUBJECTIVE EXPERIENCE AND SOCIAL-ENVIRONMENTAL FACTORS AS PREDICTORS OF TREATMENT ADHERENCE," assigned U.S. Ser. No. 62/895,567, filed Sep. 4, 2019, and claims the benefit of previously filed U.S. Provisional Patent Application entitled "CAPTURING PERSON-SPECIFIC SELF-REPORTED SUBJECTIVE EXPERIENCES AS BEHAVIORAL PREDICTORS," assigned U.S. Ser. No. 63/068,429, filed Aug. 21, 2020, both of which are fully incorporated herein by reference and for all purposes.

FIELD OF THE SUBJECT MATTER

The present subject matter relates to improved patient care. More particularly, the present subject matter relates to helping providers more productively use their time to support and improve patient treatment adherence through use of corresponding and/or related methodologies. Further, presently disclosed subject matter relates in pertinent part to advanced tools to capture, measure, and analyze self-report of subjective experiences through the use of digital applications and platforms.

BACKGROUND OF THE SUBJECT MATTER

Generally speaking, medical non-compliance is regarded by some as the most ignored national epidemic. See https.//jaoa.org/article.aspx?articleid=2538817.

The role of emotions is recognized by some as a barrier to medication adherence. See https://www.researchgate.net/publication/2592858:56

44% of polled physicians describe themselves as "burned out." Two reasons which had been noted for burnout are excessive bureaucratic tasks and too many hours spent at work. See https://www.medscape.com/slideshow/2019-lifestyle-burnout-depression-6011056

At the same time, Medicare plans a merit-based incentive payment system (MIPS) that will adjust annual physician payment by as much as 9% in 2022, based primarily on measures of quality and efficient resource use. The overall intention is to address criticism that the US health system generally rewards volume over quality of service. See http://ww.annfammed.org.

Thus, there is a generally growing shift towards value-based care, even as time pressures on healthcare providers continue to grow.

Health care market trends generally speaking tend to see on a down trend the Number of Primary Care doctors, favorable Outcomes, Doctors' time with patients, Knowing the patient, and Real-time intelligence. Elements that could be recognized as part of up trends in the field could be Demand, Costs, Non-adherence, Emotional challenges, and simply the Amount of data.

We note four key trends that suggest a new solution is needed. Those four key trends are:

1) Excessive healthcare provider workload, stress, and burnout: Not only does burnout reduce productivity and negatively impact patient care, but turnover costs healthcare systems very significant money (e.g. the costs of lost productivity when a nurse or doctor leaves, the time and money it takes to recruit & select new providers, the onboarding costs of getting new providers into place, etc.).

2) The increasing movement from volume-based medical practices to value-based care models, in which accountability for outcomes of care are increasing commensurately.

3) Complicating matters, treatment non-adherence (i.e. non-compliance, which was the traditional term for a long time, but which the term non-adherence seems to be supplanting) is an immense problem, for which many have been seeking better solutions, without immense results. "If we choose to continue accepting noncompliance as an unavoidable consequence of the public's misunderstanding or a lack of investment in their own care, we are not only allowing an ever-expanding epidemic to continue, but moving forward we will be held financially responsible." See https://jaoa.org/article.aspx?articleid=2538817.

4) There is growing literature suggesting that understanding the patient differently can help to address non-adherence, which then addresses outcomes, as adherence is a key factor in outcomes. These literatures come from the separate perspectives of emotion/behavioral science and data science (particularly, Social Determinants of Health).

To get a good sense of the sorts of work that have been done to address adherence, especially from the perspective of patient motivation, see these two articles:

Schwarzer, R., Lippke, S., & Luszczynska, A. (2011). Mechanisms of health behavior change in persons with chronic illness or disability: The health action process approach (HAPA). Rehabilitation Psychology, 56(3), 161-170.

Rich, A., Brandes, K., Mullan, B., & Hagger, M. (2015). Theory of planned behavior and adherence in chronic illness: A meta-analysis. Journal of Behavioral Medicine, 38, 673-688. doi:10.1007/s10865-015-9644-3.

See also this article:

Achtizinger, A., & Gollwitzer, P. M. (2008). Motivation and volition in the course of action. In Motivation and action (pp. 272-295). Cambridge: University Press.

Additionally, we believe that not only patients' attitudes (as can be seen in those articles) but also their emotions are of critical importance for understanding what helps to predict adherence, and subsequently to help develop prescriptive guidance. That is to say, the subjective experiences of patients are what, at the level of the patient, create significant drag and lift (referring to factors decreasing or increasing likelihood of adherence) affecting adherence. See, for example:

"Experience of negative emotions associated with medicines taking may hinder treatment adherence and should therefore not be overlooked." Easthall, C., Bhattacharya, D., & Taylor, N. J. (2013, December). The role of emotions as a barrier to medication adherence. Retrieved Jul. 8, 2019, from https://www.researchgate.net/publication/259285856 The role of emotions a bar rier to medication adherence See also Ferrer, R., Klein, W., Lerner, J. S., Reyna, V. F., & Keltner, D. (in press). Emotions and health decision-making: Extending the Appraisal Tendency Framework to Improve Health and Healthcare. In C. Roberto & I. Kawachi (Eds.), Behavioral economics and public health. Cambridge, Mass.: Harvard University Press.

Furthermore, from the data science (SDOH) side of things, this is relevant:

- 51% of respondents said they'd feel supported if their healthcare provider were to ask about their social needs, particularly related to transportation, housing, food and/or social relationships
- an additional 39% said they would feel listened to or heard in such asks
- only 10% said they'd feel annoyed or even nervous in such asks See for Example Kaiser Permanente Research: Social Needs in America. (2019, June 4). Retrieved Jul. 8, 2019, from https://about.kaisrpermanente.org/content/dam/internet/kp/comms/import/uploads/201 9/06/KP-Social-Needs-Survey-Key-Findings.pdf See also the following as to the beneficial effects of various mechanisms of support on adherence:

DiMatteo, M. R. (2007). Social support and patient adherence to medical treatment: a meta-analysis. Health Psychology 23(2), 207-218.

FIG. 1 is a prior art pie chart of determinants of overall health as published by The New England Journal of Medicine in September 2007. In a December 2019 article, Forbes magazine reported statistics that 20% of Americans manage a diagnosable mental health condition in any given year; up to 80% will manage a diagnosable mental health condition in their lifetime; and on average, individuals must wait 25 days for a psychiatry appointment—and putting off care for behavioral health needs can increase medical spend by up to 300%.

Disconnections in our society are driving an unprecedented epidemic of mental health disorders, substance abuse, violence, and chronic disease. The prime factors of this disconnection are loneliness and social isolation—the #1 chronic disease in the US—and related emotional determinants, exacerbated by social circumstances. Health providers are responding to this disconnection problem without sufficient time with the patient, useful data and metrics, or an easy way to identify, assess and manage underlying emotional and social factors.

Human experiences include moods, emotions, feelings, and other "affective states" as well as other subjective experiences, such as physical pain, attitudes, and opinions. Feelings and emotions are, for the most part, the cornerstone of all subjective experience—the color of our being in the world. Not only that, but they're the foundations of our motivations, and ultimately, our behaviors. They're fundamental to our capacities to know what is important, in what ways, and to what extents, to make decisions and connect with others. Modern research suggests that emotions are not the opposite of reason, but instead, that we practically cannot make decisions without their vital influence. There is evidence to suggest that data pertaining to specific emotions can be more informative for various purposes than data pertaining to sentiment alone.

Other subjective experiences, like pain, have their own motivational components. For example, in most cases, people across the age span are motivated to avoid, reduce, and eliminate pain, nausea, and hunger, as extremes of each can represent physical dysfunction and can contribute to functional impairments.

Various researchers approach this question from differing theoretical perspectives and with differing methodologies. However, most of them agree that emotions matter to the degree they represent internal and interpersonal communication systems that serve adaptive purposes with survival value. Across time, and varying from one theorist or model to another, such terms as emotion, feeling, affect, and mood are often used interchangeably, though arguably distinctions between them are useful, at least to scholars, clinicians, and data scientists. Furthermore, other subjective experiences—such as attitudes, opinions, judgements, and even sensory pain—are certainly significant in the human condition as shapers of behavior and signals of intentions.

Debate exists as to which emotions are most important, and indeed, whether and to what degree any should be considered universal or even "basic." However, for more than 50 years, Paul Ekman, PhD has focused on visible facial displays. His work has generated considerable evidence suggesting that at least a few emotions stand as primary candidates for universality: anger, sadness, fear, happiness, disgust, and surprise. This body of work suggests that these emotions are both easily identified and not easily confused with one another in facial displays by persons across multiple age, gender, cultural, and socio-economic backgrounds.

Ekman has determined that other emotions—although not necessarily so consistently or reliably observable or identifiable in facial expressions—are also potentially universal. These include amusement, contempt, contentedness, embarrassment, guilt, pride, relief, satisfaction, shame, and sensory pleasure.

Ira J. Roseman, PhD has proposed a model of 17 "core" emotions that are not necessarily identifiable via distinct facial expressions, but which his research suggests as being tied to specific and distinct motivational and behavioral valances. These include surprise, hope, fear, joy, relief, sadness, distress, frustration, disgust, love, dislike, anger, contempt, pride, regret, guilt, and shame.

Cognitive scientists, using Ekman's Facial Action Coding System and computerized investigational methods, have proposed a set of 21 emotions that include the six "universal" ones proposed by Ekman, but which also include additional basic and "compound" emotional expressions, including awed, appalled, hatred, happily surprised, sadly surprised, sadly angry, fearfully disgusted, disgustedly surprised, and others.

Furthermore, Lisa Feldman Barrett, PhD has argued persuasively from a constructivist viewpoint that emotions are socially constructed. She does argue that they do not exist, but that there are not necessarily any that are more basic to others, or even universal, but that there are common experiences across cultures and languages that are more or less consistently labeled with language, with variability of experience within any given label (e.g. that one might shout in anger, or remain quiet, while still labelling one's internal experience with the term "anger").

There is ample evidence pointing to the deleterious effects of poor mental health on general health, well-being, productivity, financial security, mortality risk, and trans-generational transmission of psychopathology. Further, increasing research evidence points to loneliness and social isolation as a major contributor to and artifact in depression, anxiety, substance abuse, suicide, dementia, interpersonal violence, personality disorders, and other psychiatric disorder classes. Recent evidence has compared the increased mortality risk of loneliness and social isolation to that of smoking 15 cigarettes daily, and suggests that the problem is growing in scope and severity in the U.S. and abroad.

Affective determinants as they relate to health may be defined as those subjective feelings that impact health and wellness through psychophysiological and/or psychobehavioral mechanisms. As a scientific field, such affective determinants have been studied by academicians for decades but has been stymied for two well-known obstacles:

1. a general inability to measure subjective experiences and,
2. a lack of understanding as to the correlation of various affects and subsequent impacts on psychological, behavioral and mental disorders, and chronic disease.

As referenced above, there is much evidence pointing to the deleterious effects of poor emotional health on general health and other aspects of the human condition. Trends in a variety of population health indicators paint an alarming picture; there are a few key diseases and disorders for which emotions, moods, attitudes, and other affective phenomena are direct and/or indirect risk factors. In the U.S., deaths by suicide have increased over the past 20 years. U.S. deaths from drug overdose have shown a similar trend, punctuated by the opioid crisis. Despite record spending, rates of depression in the U.S. remain alarmingly high. The annual cost of diabetes in the U.S. is staggering, even when only the impact to productivity is considered, and cardio-vascular disease remains the most severe in costs, death, and disability.

Complex processes of cognitive decision-making, emotions, socioeconomic factors, and social support all are elements that likely play a unique role in adherence for each individual patient. As can be seen from the multiple examples above, academic research has made strides in developing theoretical models of how these complex processes work to influence adherence. However, when the practicing healthcare provider makes a recommendation to a patient, they typically have very little understanding of how likely the patient is to adhere to the recommendation. Assessing internal and subjective factors experienced by the patient, such as their emotional reaction to a medical diagnosis, is beyond the scope of most healthcare providers. Moreover, even in ideal situations when providers work on multidisciplinary teams with other practitioners skilled in assessing internal/subjective factors (e.g., psychologists), the results of evaluations from these assessments are often too complex and lengthy to practically guide medical care. Further, while providers may have access to some information on the social and economic status of the patient, social and economic variables are interrelated in complex ways that preclude making good predictions based on limited information. For example, some patients living in poverty with limited access to medical care can have excellent adherence to medical recommendations whereas some wealthy patients with a range of healthcare options can struggle substantially to follow the same recommendations.

What do Payors, Providers, and People Need?
Enhanced population health assessment capacities
Enhanced population risk stratification capacities
Enhanced whole-person health strategies In other words, what's needed is reduced risks, reduced costs, and enhanced care, based on improved strategies to gather better data, from more people, more frequently—whether we're looking at entire populations, samples/subsets, or individuals.

Presently disclosed subject matter addressed solutions for such problems.

SUMMARY OF THE SUBJECT MATTER

In view of the recognized features encountered in the prior art and addressed by the present subject matter, improved apparatus and methodologies are provided for helping patients improve treatment adherence by healthcare providers productively focusing their time with the patient to know both the clinical and non-clinical factors affecting the patient's health, i.e., know the whole patient. More particularly, disclosed methodologies provide improved predictors of patient adherence by using person-specific subjective experience and social-environmental factors. Further, presently disclosed subject matter in part relates to use of person (i.e., patient)-specific subjective experience and in some embodiments social-environmental factors as well as predictors of treatment adherence.

In other respects, the presently disclosed subject matter relates in pertinent part to methodologies for capturing, measuring, storing, analyzing, and reporting data corresponding to subjective experiences, particularly such as those of patients (or in some instances others involved with care of patients or of particular patients). The presently disclosed subject matter also in pertinent part relates to affective phenomena, as fully discussed herein.

Presently disclosed subject matter in part improves connections between the patient and health provider. Through streamlining and automation, provider actionable intelligence is seamlessly passed to a provider, concerning both emotional and social determinants/factors, sometimes in a composite-style scoring format. In some embodiments, presently disclosed subject matter also may suggest and monitor interventions that manage any obstacles a particular patient may have to achieving better health. Use of machine learning capabilities identify the most effective interventions over time and enable artificial intelligence to participate in prescribing best practices to addressing risks determined through presently disclosed assessments of emotional determinants.

These models point to several emotions with some consistency, while also leaving room for disagreement and thus, expansion of science. The transforming icon technology, via presently disclosed Scale Builder subject matter, allows users to create transforming or shape-shifting icons that can represent each of these emotions and expressions, along with other subjective human experiences. Those others can include theoretical, practical, cultural, linguistic, and popular variants, such as "OMG" and "SRSLY?" along with other arguably more basic experiences such as hunger, dizziness, fatigue, felt sense of hot/cold, and sensory pain.

Other advantages of various embodiments of presently disclosed subject matter relate to efficient, expedient distribution, collection, scoring, and analysis of relevant data factors. Further facets may in some instances relate to enhanced tracking and monitoring capacities, as well as providing providers and caregivers with digestible, actionable interpretations of data. Further potential results relate in pertinent part to better connections to supports that can address the identified risks and needs. The bottomline relates in part to better intelligence as to which supports work best for whom, when, and in what doses.

The user interface's various physical facets (e.g. color, shape, shading, opacity, rate of change in response to user input, etc.) and the variety of means and mechanisms by which user input might be registered give the presently disclosed technology an extraordinary degree of flexibility for applications to an extraordinary range of phenomena, and a similarly high degree of flexibility for tailoring to population, sub-population, and individuals' characteristics.

Inasmuch as the user interfaces are designed to represent subjective phenomena and mental phenomena via an "affect mirror" interaction, the technology requires very little by way of verbal or written prompts, and therefore offers a prime opportunity for deployments that are arguably more culture-fair and language-agnostic than other, more traditional methods. Additionally, it is demonstrably easy for youth and children to use effectively. Thus, it has potentially global applicability.

Transforming icon technology is a user-controlled, dynamically-adjustable visual medium designed to capture, measure, and convey a wide variety of subjective experiences including, but not necessarily limited to, emotions, moods, feelings, sentiments, attitudes, opinions, judgements, preferences, bodily sensations, and mental phenomena such as visual acuity and information processing speed. It is also designed to be highly engaging. These capacities make the technology particularly interesting for research and application within clinical, healthcare, and wellness settings.

The quantification of such subjective experiences and mental phenomena yields truly continuous (versus discrete) interval or ratio data, allowing a high degree of granularity of measurement, as well as useful metadata of various types, including e.g. time-on-task, which themselves can be used combinatorially with the primary measures and independently.

We use the term "shape-shifting or transforming icons" to refer to proprietary digitally-rendered graphical user interfaces (GUIs) comprised of facial expressions and/or other percepts that are intended to represent subjective experiences including, but not necessarily limited to, emotions, feelings, affects, moods, sentiments, attitudes, judgments, and opinions, and which yield scalable data corresponding to those experiences.

Shape-shifting icons combine the attributes of affect displays and visual analogue scales in digital form, and they reflect contributions from the fields of cognitive science, neuropsychology, affect theory, computer science, developmental psychology, and others. More generically referred to as transformable or shape-shiftable objects, they are created and rendered via proprietary processes that provide for their generation, display, data production, storage, reporting, and data analysis. One example of such technology for measuring user-controlled input is provided in part by U.S. Pat. No. 9,959,011, the complete disclosure of which is incorporated herein by reference and for all purposes.

We refer herein to the collective software system of front-end and back-end elements to accomplish such characteristics and functions as the transforming icon Platform. For practical purposes, we use transforming icon technology in part to refer to the platform, and use the references transforming icons or shape-shifting icons to refer to a specific images that serve as GUI's. Individual shape-shifting icons are referred to with the singular, transforming icon.

Use of transforming icon technology in healthcare affords us the ability to more efficiently and effectively measure emotions, moods, attitudes, and other affective phenomena compared to traditional questionnaires, partially due to higher levels of engagement from those surveys.

People naturally read facial expressions. Non-verbal communications are at the essence of human development—witness the communication between mother and infant. As we mature, our ability to read facial expressions and other symbols are enhanced.

With transforming icon technology, users can capture and measure affective phenomena in a way that rises above linguistic and cultural constraints encountered with traditional questionnaires.

The presently disclosed Platform facilitates investigation for assessment and intervention by administering the transforming icon technology surveys and providing sophisticated analytics that may correlate various affective phenomena (for example, loneliness, stress, anxiety, depression, pain, malaise) to each other as well as clinical and sub clinical disorders. Such correlation is validated by factually establishing that we are measuring what we intend to, by comparing transforming icon technology questions to traditional questionnaires and scoring methods.

Presently disclosed subject matter may use such results to create an Index Score, which could then in some instances allow the science to be applied, through use in various products available, such as SaaS products, for addressing areas such as Diabetes management, Orthopedics, Cardiology, Oncology, Stroke, as well as retail applications (such as for drug stores and insurance companies); and Accountable Care Organizations and data applications through electronic medical records or healthcare records.

We believe it is critical to better understand what we are calling various affective phenomena when it comes to affective factors or determinants and how they relate to individual and collective (population) health, conceptualized and measured as subjective experiences of loneliness, depression, anxiety, stress, pain, and malaise (which can include fatigue and daytime dysfunction due to poor sleep quality). This is because of the dual pathways by which these subjective experiences can exert direct (psychophysiological) and indirect (psychobehavioral) negative effects on health, well-being, and consequent life management and functioning.

As psychedelics and other atypical drugs including ketamine are rapidly generating new interest research as potentially ground-breaking interventions against a host of psychiatric conditions, we believe it is critical to capture and measure these affective factors along with social factors or determinants relative to health, to help build—in an efficient, engaging, real-time manner—a more complete picture of the people seeking these treatments before, during, and after in-clinic interventions. This could include objective measurement of subjective experiences during drug administration and during psychotherapy sessions. This more complete picture, developed without the tedium, language/cultural obstacles, and inconvenience typically associated with traditional instruments, can expedite communications among healthcare professionals (including mental health clinicians), between providers and patients, and even between patients and the peer supports that can serve as needed adjuncts to help address their multiple personal and psychosocial needs. And, these are important measures to track among those personally affected by those with mental health challenges, including in particular, spouses, children, and other loved ones.

Additionally, these factors provide the foundation for exploring the varieties of supports available from healthcare providers, paraprofessionals, peers, and new Artificial Intelligence-based agents, such as chatbots and voice-mediated agents, and their impacts in the service of prevention, augmentation of clinic-based interventions (drugs, psychotherapy, etc.), at both the individual and population levels, to increase the speed with which we can identify, develop, leverage, deliver to and connect patients with those supports.

The issue of non-adherence is addressable. The role of patients' emotional characteristics in adherence is measurable. The impact of the coordinated care team is leverageable, based on a key of knowing the patient differently.

In some embodiments, methodologies combine emotion and data sciences with machine learning to help patients improve treatment adherence and healthcare providers productively use their time with patients to better know the whole patient. Patient-specific data is obtained regarding emotional and social factors, the data results from which are analyzed to determine, in effect, a Likelihood To Adhere (LTA) Index Score, to indicate probability of adherence to a prescribed treatment plan and cohorts (groupings) for the given patient. Internal/subjective factors are judged by means of self-report measures (derived from such fields as personality psychology, emotion science, or cognitive science), while external/social factors are assessed by various means of intelligence gathering. The integration of these relevant factors leveraged with machine learning powers the capability and reliability of predicting a patient's likelihood to adhere to the prescribed treatment plan.

One exemplary embodiment makes use of interactions among emotional, health, and social characteristics, using graphical interfaces to capture and measure subjective experiences. Emotional characteristics may include perception and intensity in each of categories such as sickness versus wellness, stress, depression, anxiety, pain, and feelings about most recent health provider/staff interaction (with determined intensity for choices of Delighted, Satisfied, Meh, Disappointed, Frustrated). Each characteristic can measure a potential obstacle to adherence, and become a form of screening for various constructs to which primary care physicians should then attend.

Such consideration of affective determinants or factors, augmented by social factors or determinants, help to identify:

1. Psychobehavioral risk factors for mental health challenges, chronic disease onset/progression, and non-adherence;
2. Psychophysiological risk factors for chronic disease onset/progression; and
3. Environmental/circumstantial risk factors for chronic disease onset/progression and treatment non-adherence.

Other exemplary advantages of practicing presently disclosed subject matter include, but are not limited to:

1. A standardized data collection method and procedure applicable across populations and sites, with potential world-wide scope;
2. A more engaging user interface that enhances data collection rates and frequency of collection;
3. Improved tracking of which supports people access, when, and how often, with intra-individual and inter-individual trend analysis;
4. The capacity to tie in additional data sources (e.g. from claims, EHR's, etc.) and advanced analytics capacities, augmented by machine learning;
5. Improved data flow and communications across an ecosystem of supports incorporating providers, para-professionals, peers-based supports, and AI/technology supports (e.g. chatbots); and
6. A robust, flexible SaaS platform that provides for everything mentioned above, meeting high standards for simplicity, engagement, expediency, comprehensiveness, and utility.

One exemplary embodiment of presently disclosed subject matter relates in pertinent part to methodology for predictively determining a patient's likelihood to adhere to a healthcare treatment plan for such patient. In particular, such methodology may preferably comprise creating a survey comprising a plurality of survey items related to selected determined obstacles to adherence; interactively conducting the survey for a given patient by having the patient use a movable feature of a graphical interface to respectively capture and definitively measure the patient's subjective experiences for each of the plurality of survey items, to form a set of data for the given patient for the corresponding plurality of survey items; and assessing the patient's set of data to determine a relative score for such patient for likelihood to adhere to a healthcare treatment plan.

In some exemplary embodiments of the foregoing methodology, such graphical interface may comprise a respective shape-shifting icon for at least one of the survey items and a movable element for the patient to continuously manipulate the shape-shifting icon through a range of appearances designed to correlate with the intensity of the patient's feelings in response to a survey item. Further, in some such instances the definitive measurement captured with each icon may correspond directly to the final point of continuous manipulation established by the patient through such range of appearances in response to a particular survey item. In additional of some such instances, such shape-shifting icons may be pre-validated for a selected population of patients in which the given patient is a member, to validate that each icon and its range of appearances represents the subject matter of its associated item and attendant range of intensities thereof.

In yet other alternative exemplary embodiments of such methodology, such graphical interface may comprise patient-adjustable dynamically-manipulatable digital graphic displays for each of the survey items, rendering scaled values to capture and definitively measure subjective experiences by having the patient use a movable bar to manipulate at least one of each respective icon so that it reflects how the patient feels in response to each item.

In still other alternative exemplary embodiments of such methodology, assessing the patient's set of data may include establishing a predictive score for the given patient indexed relative to ranges of scoring of sets of data for responses to items involving the same shape-shifting icons as have been used in the survey for the given patient and pre-validated for a selected population of patients in which the given patient is a member.

Per other variations of the foregoing, assessing the patient's set of data may include establishing one of a relatively high, medium, or low probability of adherence to a healthcare treatment plan for the given patient.

For other alternatives, assessing the patient's set of data may include establishing a specific score within an indexed range to relatively assess the probability of adherence to a healthcare treatment plan for the given patient. For some such alternatives, such indexed range may comprise a scaled range from between 0 and 100.

In some alternative methodologies, the indexed range may comprise a scaled and normalized range from between 0 and a predetermined top scale number. In some such instances, the predetermined top scale number falls into a range from 1 to 100.

Yet other alternative exemplary embodiments of such methodology may include reporting the determined relative score to at least one of the given patient, healthcare staff supporting the patient, researchers, administrators, payors, and supportive associates of the given patient. In some alternative such embodiments, such methodology may include subsequently interactively conducting the same or a different survey for the given patient at a later point in time, and reporting an updated relative score to at least one of the given patient, healthcare staff supporting the patient, researchers, administrators, payors, and supportive associates of the given patient.

Still other presently disclosed exemplary variations of the foregoing may include creating a database of measures of the patient's health status indicators and external social and economic variables to likelihood of adherence, to form a set of fact-based data for the given participant; and collectively assessing the patient's internal self-reported data and fact-based data to determine a relative score for the given patient for likelihood to adhere to a healthcare treatment plan for the given patient. In some such instances, the patient's health status indicators may include at least one of body mass index (BMI), blood A1c levels, and Rx fill/refill data for the given patient.

For yet other alternatives of the foregoing methodology, the healthcare treatment plan may comprise at least one of a plan of treatment for a particular condition of a given patient and a wellness activities plan for a given patient. For others, the items may include at least one of a question, an image, a statement, a sound bite, and a video file presented to the patient for capture of the patient's subjective response thereto.

In yet other alternatives of the foregoing methodology, assessing the patient's set of data may include establishing a specific score within an indexed range to relatively assess the probability of adherence to a healthcare treatment plan and cohorts for the given patient.

Yet another exemplary methodology embodiment in accordance with presently disclosed subject matter may include in pertinent part methodology for predictively determining a participant's likelihood to adhere to an activity plan for such participant. Such further alternative methodology preferably comprises interactively conducting a survey for a given participant by having the participant use a movable feature of a graphical interface to respectively capture and definitively measure the participant's self-reported internal subjective feelings in response to a plurality of survey items concerning affect-based variables to likelihood of adherence, to form a set of internal self-reported data for the given participant; creating a database of measures of the participant's external social and economic variables to likelihood of adherence, to form a set of external fact-based data for the given participant; and collectively assessing the participant's internal self-reported data and external fact-based data to determine a relative score for such participant for likelihood to adhere to an activity plan.

For some other such exemplary methodology embodiments, creating a database of measures may further include creating a database of measures of the participant's external social and economic variables, and external environment variables affecting a patient's likelihood of adherence, to form the set of external fact-based data for the given participant. In some such instances, the external social and economic variables and external variables to likelihood of adherence for a patient may comprise social/economic/environmental factors experienced by an individual patient that negatively impact medical treatment plan adherence, including at least one of low socioeconomic status, low health literacy, low levels of education, low levels of social support, unemployment, housing instability, poor environmental conditions, family dysfunction, barriers with transportation to medical care, high medication costs, and negative cultural beliefs about medical treatment.

For yet other such exemplary methodology embodiments, such affect-based variables may comprise determined obstacles to achievement of activities in an activity plan; and such graphical interface may comprise dynamically-manipulatable digital graphic displays with at least one icon for each of the survey items, rendering scaled values to capture and measure subjective experiences by having the participant use a movable bar to manipulate at least one of each respective icon so that it reflects the intensity of how the participant feels in response to each item. In some such instances, such digital graphic displays may comprise a plurality of shape-shifting icons with at least one icon for each respective survey item and a movable element for the participant to continuously manipulate a shape-shifting icon through a range of appearances designed to correlate with the intensity of the participant's feelings in response to a survey item, with the appearances of the shape-shifting icons pre-validated for a population of participants in which the given participant is a member, to validate that each icon represents the subject matter of its associated item and attendant range of intensities thereof.

For other exemplary variations of the foregoing methodology, collectively assessing the participant's internal self-reported data and external fact-based data may include establishing one of a relatively high, medium, or low probability for such participant for likelihood to adhere to an activity plan.

In yet others, collectively assessing the participant's internal self-reported data and external fact-based data may include establishing a specific score within an indexed range to relatively assess the probability for such participant for likelihood to adhere to an activity plan. In some such instances, such indexed range may comprise a scaled range from between 0 and 100.

In some alternative methodologies, the indexed range may comprise a scaled and normalized range from between 0 and a predetermined top scale number. In some such instances, the predetermined top scale number falls into a range from 1 to 100.

In other variations of the foregoing exemplary methodology, such participant may comprise a potential consumer for a given product, and the survey items may relate to a particular product or service of potential interest to the potential consumer, as part of evaluating customer experiences or conducting consumer research relative to such particular product or service.

In some other alternatives of the foregoing, the participant may comprise a patient and the activity plan may comprise a health treatment plan for the patient. In some such instances, such methodology may further include subsequently interactively conducting the same or a different survey for the given patient at a later point in time, and reporting an updated relative score to at least one of the given patient, healthcare staff supporting the patient, researchers, administrators, payors, and supportive associates of the given patient.

In yet other alternative instances, the external social and economic variables to likelihood of adherence for a patient comprise social/economic factors experienced by an individual patient that negatively impact medical treatment plan adherence, may include at least one of low socioeconomic status, low health literacy, low levels of education, low levels of social support, unemployment, housing instability, family dysfunction, barriers with transportation to medical care, high medication costs, and negative cultural beliefs about medical treatment.

In still other alternative instances, the internal subjective feelings which may be variables to likelihood of adherence for a patient may include self-reported felt sense and intensity thereof for at least one of wellness versus illness, stress, depression, anxiety, pain, and loneliness of the patient. In some such instances, the internal subjective feelings may further include a patient's self-reported sense and intensity of satisfaction with the patient's most recent health provider/staff interaction.

For yet other alternatives of the foregoing, the survey items in some instances may include at least one of a question, an image, a statement, a sound bite, and a video file presented to the participant for capture of the participant's subjective response thereto.

The presently disclosed subject matter equally relates as much to corresponding and related systems and apparatus as it does the exemplary methodologies included herewith. One exemplary such system relates in pertinent part to a system for predictively determining a given patient's likelihood to adhere to a healthcare treatment plan for such patient. Such an exemplary system preferably comprises a memory; a display; and a processor. Such processor is preferably coupled to the memory which is programmed with executable instructions. Such instructions may include a patient survey comprising a plurality of survey items to be administered to a given patient and related to selected determined obstacles to adherence to a healthcare treatment plan for such patient; a patient graphical interface comprising dynamically-manipulatable digital graphic shape-shifting icons for such patient to view on such display, and to capture and definitively measure subjective experiences thereof by such patient by having such patient use a movable feature to manipulate the appearance of each respective icon through a range of appearances thereof so that it reflects the self-reported intensity of how such patient feels in response to each item of the patient survey; and an assessing component, for assessing such patient's set of self-reported responses to determine a relative score for such patient for likelihood to adhere to a healthcare treatment plan.

Per further alternative exemplary embodiments of the foregoing, such system may be implemented via a hardware and software platform comprising a plurality of network-based non-transitory storage devices, servers, and processors, which may be accessible by authorized users. In some such alternatives, such system may include at least one network-based non-transitory storage device for being accessed by authorized users, for the update and storage therein of data on at least one particular patient concerning at least one of background external health, social, and economic variables to likelihood of adherence for such particular patient.

In other alternatives of the foregoing, such system may include at least one network-based non-transitory storage device for being accessed by at least one particular patient, for the update and storage therein of data on at least one of definitively measured subjective experiences for such particular patient in response to at least one item of the patient survey.

In yet other presently disclosed variations, such a system may include at least one network-based non-transitory storage device for being accessed by at least one particular patient, for the update and storage therein of data on at least one of definitively measured subjective experiences for such particular patient in response to at least one item of the patient survey; and such assessing component may be further operative for collectively assessing such patient's set of responses along with stored data on such patient concerning background external health, social, and economic variables to likelihood of adherence, to determine a relative score for such patient for likelihood to adhere to a healthcare treatment plan. In some such variations, such assessing component may be further operative for collectively assessing such patient's set of self-reported responses normalized relative to stored data of anonymized results from a plurality of other patients with common or similar background data.

In other variations thereof, such assessing component may be further operative for storing on at least one network-based non-transitory storage device the self-reported responses and relative score for such patient for likelihood to adhere to a healthcare treatment plan, to be accessed by authorized users. In some such variations, such assessing component may be further operative for storing on such at least one network-based non-transitory storage device the self-reported responses and relative scores for such patient, based on repeated administrations of the same or a different patient survey to such patient, for likelihood to adhere to a healthcare treatment plan data for such patient, to be accessed by authorized users.

Still for further presently disclosed alternatives of such system, such system in some instances may further include a reporting device for preparing a report of data otherwise stored on at least one network-based non-transitory storage device regarding the self-reported responses and relative score for such patient for likelihood to adhere to a healthcare treatment plan, and for transmitting the report to selected entities. In some such alternatives, such selected entities may comprise at least one of a given patient, healthcare staff supporting the given patient, researchers, administrators, payors, and supportive associates of the given patient. In some of those instances, such reporting device may be operative for preparing a report covering time periods determined by the selected entity to receive the report.

Another presently disclosed variation relates to such a system wherein such patient movable feature may comprise a patient movable bar to manipulate at least one of each respective icon so that it reflects how the patient feels in response to each item.

For other presently disclosed alternatives, such shape-shifting icons may be pre-validated for a selected population of patients in which the given patient is a member, to validate that each icon and its range of appearances represents the subject matter of its associated item and attendant range of intensities thereof. For some such variations, such shape-shifting icons may be pre-validated through an iterative icon design process which focuses on a patient's perceived resonance between an icon and the corresponding subject matter being surveyed through use of such icon. For yet others, such iterative icon design process may include use of a forced-choice validation engine paradigm to study the correlation between an icon design and the subject matter to be surveyed through use of such icon. For still others, such iterative icon design process further may include use of an intensity rating validation paradigm to study the correlation between an icon design and the range of intensities of a patient's feelings to be represented by such icon.

In some other alternatives of such presently disclosed systems, such healthcare treatment plan may comprise at least one of a plan of treatment for a particular condition of a given patient and a wellness activities plan for a given patient. In other alternatives, such shape-shifting icons may respectively comprise icons with changing aspects each may include at least one of construction, display, and use may include size, color, shape, opacity, and data input methods. In still others, such patient graphical interface may capture and definitively measure subjective experiences by rendering scaled values by having the patient use a movable bar to manipulate at least one of each respective icon so that it reflects how the patient feels in response to each item.

For some other alternative presently disclosed systems, such relative score may include one of a relatively high, medium, or low likelihood to adhere to a healthcare treatment plan for such patient.

In yet other alternatives, such relative score may include a specific score within an indexed range to relatively assess the likelihood to adhere to a healthcare treatment plan for such patient. In some such alternatives, such indexed range may comprise a scaled range from between 0 and 100. For other variations of presently disclosed exemplary systems, the survey items may include at least one of a question, an image, a statement, a sound bite, and a video file presented to the patient for capture of the patient's subjective response thereto.

In some alternative systems, the indexed range may comprise a scaled and normalized range from between 0 and a predetermined top scale number. In some such instances, the predetermined top scale number falls into a range from 1 to 100.

Additional objects and advantages of the present subject matter are set forth in, or will be apparent to, those of ordinary skill in the art from the detailed description herein. Also, it should be further appreciated that modifications and variations to the specifically illustrated, referred and discussed features, elements, and steps hereof may be practiced in various embodiments, uses, and practices of the present subject matter without departing from the spirit and scope of the subject matter. Variations may include, but are not limited to, substitution of equivalent means, features, or steps for those illustrated, referenced, or discussed, and the functional, operational, or positional reversal of various parts, features, steps, or the like.

Still further, it is to be understood that different embodiments, as well as different presently preferred embodiments, of the present subject matter may include various combinations or configurations of presently disclosed features, steps, or elements, or their equivalents (including combinations of features, parts, or steps or configurations thereof not expressly shown in the figures or stated in the detailed description of such figures). Additional embodiments of the present subject matter, not necessarily expressed in the summarized section, may include and incorporate various combinations of aspects of features, components, or steps referenced in the summarized objects above, and/or other features, components, or steps as otherwise discussed in this application. Those of ordinary skill in the art will better appreciate the features and aspects of such embodiments, and others, upon review of the remainder of the specification, and will appreciate that the present subject matter applies equally to corresponding methodologies as associated with practice of any of the present exemplary devices, and vice versa.

BRIEF DESCRIPTION OF THE DRAWINGS

A full and enabling disclosure of the present subject matter, including the best mode thereof, directed to one of ordinary skill in the art, is set forth in the specification, which makes reference to the appended figures, in which:

FIGS. 3A and 3B represent respective exemplary Health Characteristic components of the exemplary survey embodiment referenced per FIG. 2A;

FIGS. 4A through 4H represent respective exemplary Social Characteristic components of the exemplary survey embodiment referenced per FIG. 2A;

FIG. 5C is a chart of exemplary ranges of scoring, using color coding, that could be used for reporting determined likelihood of adherence per some embodiments of presently disclosed subject matter;

FIG. 11 illustrates a chart representing the correlation (r) with number of behaviors for positive and negative valences for each of seven emotions tested vis-àvis the subject matter represented by FIGS. 10A and 10B;

FIG. 15A is a self-explanatory example of a presently disclosed Preliminary Validation Engine user interface embodiment, allowing testing subjects (respondents) to register qualitatively whether, and to what extent, a given design proposal appeared to represent a construct;

Figure 1:
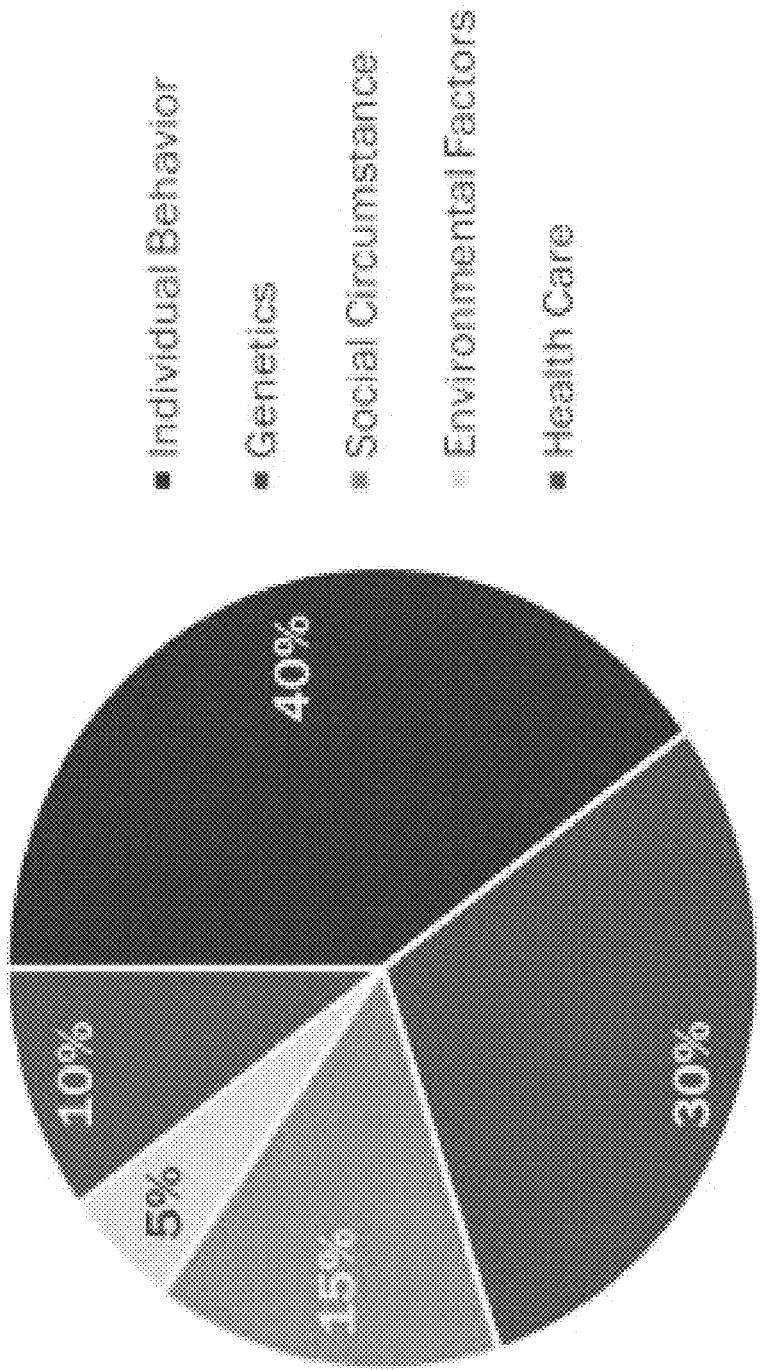
FIG. 1 is a prior art pie chart of determinants of overall health as published by The New England Journal of Medicine.

Repeat use of reference characters throughout the present specification and appended drawings is intended to represent same or analogous features, elements, or steps of the present subject matter.

DETAILED DESCRIPTION OF THE PREFERRED EMBODIMENTS

As discussed in the Summary of the Subject Matter section, the present subject matter is particularly concerned with improved apparatus and methodology to use person-specific subjective experience and social-environmental factors as predictors of treatment adherence.

Selected combinations of aspects of the disclosed technology correspond to a plurality of different embodiments of the present subject matter. It should be noted that each of the exemplary embodiments presented and discussed herein should not insinuate limitations of the present subject matter. Features or steps illustrated or described as part of one Embodiment may be used in combination with aspects of another embodiment to yield yet further embodiments. Additionally, certain features may be interchanged with similar devices, features, or steps not expressly mentioned which perform the same or similar function.

One present object in part is to innovatively combine emotion science, data science, and machine learning to help patients improve treatment adherence and healthcare providers productively use their time with patients to support and improve patient treatment adherence. The presently disclosed approach is to recognize that emotional factors or determinants and social determinants or factors considered respectively in part or together can improve prediction of patient's likelihood of adhering to their treatment plans. In such context, data gathering, analysis, and summation is streamlined and automated to provide more timely, more comprehensive, and more actionable insights while saving the physician time. This can be addressed in part following this approach for some embodiments (Table 1):

TABLE 1

$[x_1 + y_2] + y = z$
EDoA + SDoA supports adherence

Social Support Deficits as a Contributor to Non-Adherence

A final area that has emerged as important for consideration in understanding the patient's medical adherence is the role of social support (DiMatteo, 2004). Supportive people in patients' lives, including significant others, family members, and friends can promote adherence when these people give the patient practical assistance, such as reminders to take one's medication, transportation to appointments, or encouragement to maintain a healthy diet. Supportive others have also been shown to increase adherence when they encourage optimism and self-efficacy on the part of the patient. Further, social support can serve as a buffer between the emotions one experiences related to an illness and their likelihood of adherence, for instance social support can reduce risk for patient depression (Liu et al., 2017). In a systematic review of 122 studies on the link between social support and patient adherence to medical treatment, DiMatteo (2004) found that both practical and emotional forms of social support were predictive of a greater level of adherence for a wide variety of diseases; recovery from illness and injury; and health maintenance.

As a standard for adherence management, presently disclosed subject matter in part involves establishing in effect an Adherence Score through use of analysis of Key Drivers, and seek to provide techniques for improving scores.

What are Affective Determinants when Considering Health, and What are Some Examples?

Affective determinants or factors relative to health represent a broad class of affective phenomena including (but not limited to) emotions, moods, attitudes, feelings, and even opinions that are subjective experiences and that influence disease onset, development, and progression in either positive (i.e. protective) or negative (i.e. risk-enhancing) ways. These effects can occur through psychobehavioral channels, representing, for example, influences on people's motivation, intention, volition (effort), and determination (behavioral resilience) in health behaviors. The effects can also occur through psychophysiological channels, as when elevated stress-induced cortisol negatively affects brain cells critical to memory functions or increases systemic inflammation.

Stress

Chronic stress, in particular, can disturb immune, digestive, cardiovascular, sleep, and reproductive systems, and has been identified as a risk factor for cardiovascular disease, hypertension, heart failure, diabetes, obesity, and diminished memory and cognitive capacities. It is a major contributor to alcohol and drug abuse, poor diet, physical inactivity, and can contribute to instances of interpersonal violence. It has been implicated in poor medication treatment adherence.

Anxiety

Anxiety has been implicated in several chronic illnesses, including heart disease, chronic respiratory disorders, and gastrointestinal conditions. Like stress, chronic anxiety and worry is a contributing factor in alcohol and drug abuse, smoking, overeating, and has been implicated in poor medication treatment adherence.

Loneliness

A stressor unto itself, and a common risk factor for depression, loneliness has been linked to alcoholism and drug abuse, antisocial behaviors, cardiovascular disease, hypertension, obesity, inflammatory disease, stroke, suicide, and diminished memory and cognitive capacities; it has been identified as a potential risk factor for Dementia of the Alzheimer's Type (DAT).

Irritability

Irritability has been linked with greater cardiovascular reactivity to stress, reduced quality of life, greater risk and persistence of depression, heightened risk of suicide, and lower educational achievement. Irritability can itself be a cause of stressful interpersonal events and may point to bipolar mood disorder presence or development, particularly if seen with elevated energy. It may occur alongside depressive symptoms or entirely separately.

Depression

Depression can contribute to and exacerbate pain and pain-related conditions, and has been identified as an independent risk factor for cardiovascular disease, heart failure, coronary heart disease, and gastrointestinal problems. It has been linked to inflammatory conditions and autoimmune disorders, including Type 2 diabetes. The sleep dysfunctions frequently associated with depression can contribute to hypertension. Depression is a leading contributor to alcohol and drug abuse, as well as suicide. It's also a leading cause of physical inactivity and has been implicated in poor medication treatment adherence.

Those are but a few examples of affective factors. Presently disclosed subject matter provides the means to assess feelings of Illness and Pain as well. Additional measures, using the presently disclosed technology, can be validated, such as for Fatigue/Energy Level.

How Can We Assess these Factors Efficiently, Effectively, and with High Engagement?

The presently disclosed subject matter makes use of transforming icon technology to capture and measure these constructs quickly. They are dynamic, user-adjustable graphic images that allow people to "dial in" the type and intensities of their emotions, moods, feelings, attitudes, and other affective phenomena, and do not require people to try to quantify their feelings' intensities—the transforming icon technology does that for them.

The transforming icon technology is unique in providing an engaging graphical interface to provide clear, concise, and efficient data capture based on our natural capacity to "see" the type and intensity of one's experiences in the interface, which can be adjusted until a moment of peak resonance is found. Quantification of the registered type and intensity of the experience occurs in the background.

Such shape-shifting icons offer the user the opportunity to "see" a depiction that most closely approximates and represents his/her subjective experience, and to tailor it for accuracy, offering a more direct (i.e. less analogue) opportunity for communication of otherwise difficult-to-quantify internal states and experiences.

Shape-shifting icons have the benefits of being
Efficient—they take very little time to complete
Engaging—they're demonstrated to be preferred over traditional Q & A methods
Effective—they demonstrate very strong correlations with traditional measures.

Per presently disclosed subject matter, Support is also a key to adherence. Essentially, there are variables that help to explain differences between people and within people across time, that have not been adequately discovered, understood, integrated, or leveraged toward the goal of increasing treatment adherence across many disease states, treatment activities, and populations. These variables can be referred to as factors, which fall into two domains—internal/subjective, and external/social. The former can be measured by means of self-report measures, and that latter, by means of intelligence gathering via a variety of mechanisms. The former can be derived from such fields as personality psychology, emotion science, cognitive science, and others. The latter can also be measured, and may be derived from what are referred to as social factors or determinants relative to health.

Many of the unique social/economic factors experienced by an individual patient that influence medical adherence can be assessed without asking the patient to describe their subjective experience. Such social factors that negatively impact medical adherence include:
Low socioeconomic status,
Low health literacy,
Low levels of education,
Low levels of social support,
Unemployment,
Housing instability,
Family dysfunction,
Barriers with transportation to medical care,
High medication costs, and
Negative cultural beliefs about medical treatment Furthermore, the internal/subjective variables can be broadly construed as occupying three major domains—emotions/moods, attitudes, and an inclusive category we reference as Other Subjective Factors, which can include (non-exhaustively) defense mechanisms, needs (e.g. need for Power, need for Affiliation, etc.), locus of control, and proximal and distal goals.

This interactive, recursive relationship between the person and their environment is a primary focus, in building a predictive model regarding individuals' likelihood to adhere to treatment across the healthcare journey. We refer to this focus as the patient in situ.

Relatedly, given the critical role of healthcare providers in helping to determine courses of care, who are held accountable for monitoring patient progress and supporting patient outcomes, and who are under increasing stress to provide quality care in a changing and in many ways dysfunctional healthcare environment, we also hold that focus on understanding the provider in situ may also be a significant focus of our efforts. The presently disclosed subject matter helps to improve healthcare outcomes by tackling the immense problem of treatment non-adherence (a.k.a. non-compliance).

One component of presently disclosed strategy for some embodiments is to help improve treatment adherence by supporting healthcare teams to support their patients' adherence success. Such strategy component is designed to help care teams to know their patients differently, by automating and streamlining the process of proving actionable insights to increase lift and reduce drag in adherence. Presently disclosed subject matter does this by combining behavioral science with data science, augmented by machine learning, to deliver products that enhance patients' and providers' chances for success while helping to make the providers' jobs easier. Such approach puts into practice the idea of "more success, less stress."

Presently disclosed subject matter in part is for healthcare providers to feel better about their work, and thus less prone to burnout, and more prone to empathizing with their patients, especially the ones with chronic illnesses and who have difficulty adhering to treatment plans. One audience for this subject matter may be healthcare practice owners and healthcare system administrators.

The present methodology in part, in a nutshell, is to (metaphorically) take an hour's worth (or more) of a psychologist's interviewing/testing time, and compress the learning that could come from that into a simple, less-than-one-page report that could provide healthcare providers (both the physicians and their team members) highly actionable information that they otherwise might not have access to, including something which in effect is a Likelihood To Adhere (LTA) Index Score—a composite score representing varying likelihoods of adherence. For example only, and not intended as limiting, we may in some instances use High, Medium, and Low probability of adherence, and in other instances other strata or other numbers of strata (and either absolute or relative) may be established.

Two primary sub-factors contributing to that assessment are:
Evaluation of the emotional factors or determinants and
Intelligence on social factors or determinants.

One approach for some embodiments is for our predictive analytics modeling (likelihood to adhere, i.e. LTA) to be situated within an Adherence Support Protocol, which may advise/prescribe care team coordination and activities to reduce drags & augment lifts. This might be coupled with a Can Do Health Adherence Support Initiative, which may be social media-based. For example, a Can Do Health smartphone app might be a potential embodiment, to compliment both the Protocol and the Initiative.

One embodiment may relate to an a minimal product or embodiment in the form of a scale rating some obstacles to adherence, for example, comprised of only six items or questions surveyed:
1) felt sense (intensity) of wellness vs. illness
2) felt sense (intensity) of stress
3) felt sense (intensity) of depression
4) felt sense (intensity) of anxiety
5) felt sense (intensity) of pain
6) felt experience of emotion (type and intensity) regarding one's most recent experience with a healthcare provider or his/her staff.

In some embodiments, each of these can measure a potential obstacle to adherence, and each represents information in the form of screening for various constructs that primary care physicians (a primary use case for presently disclosed subject matter) should attend to not only to help reduce obstacles to adherence, but in the service of their patients more generally and to monitor the health of their practices.

Another presently disclosed exemplary embodiment may make use of interactions among emotional, health, and social characteristics, while using graphical interfaces to capture and measure subjective experiences.

In particular, emotional factors (checking intensity in each category) may cover:
1. Sick/well
2. stressed
3. depressed
4. anxious
5. pain
6. Feelings about most recent health provider/staff interaction (intensity for choices of Delighted, Satisfied, Meh, Disappointed, Frustrated)

Health factors may be covered in a few additional questions or items, such as inquiries 7-11 of an exemplary survey embodiment represented in the present Figures. Social factors may be covered in a relatively larger number of additional questions, such as inquiries 12-34 of an exemplary survey embodiment of the present Figures.

Figure 2A:
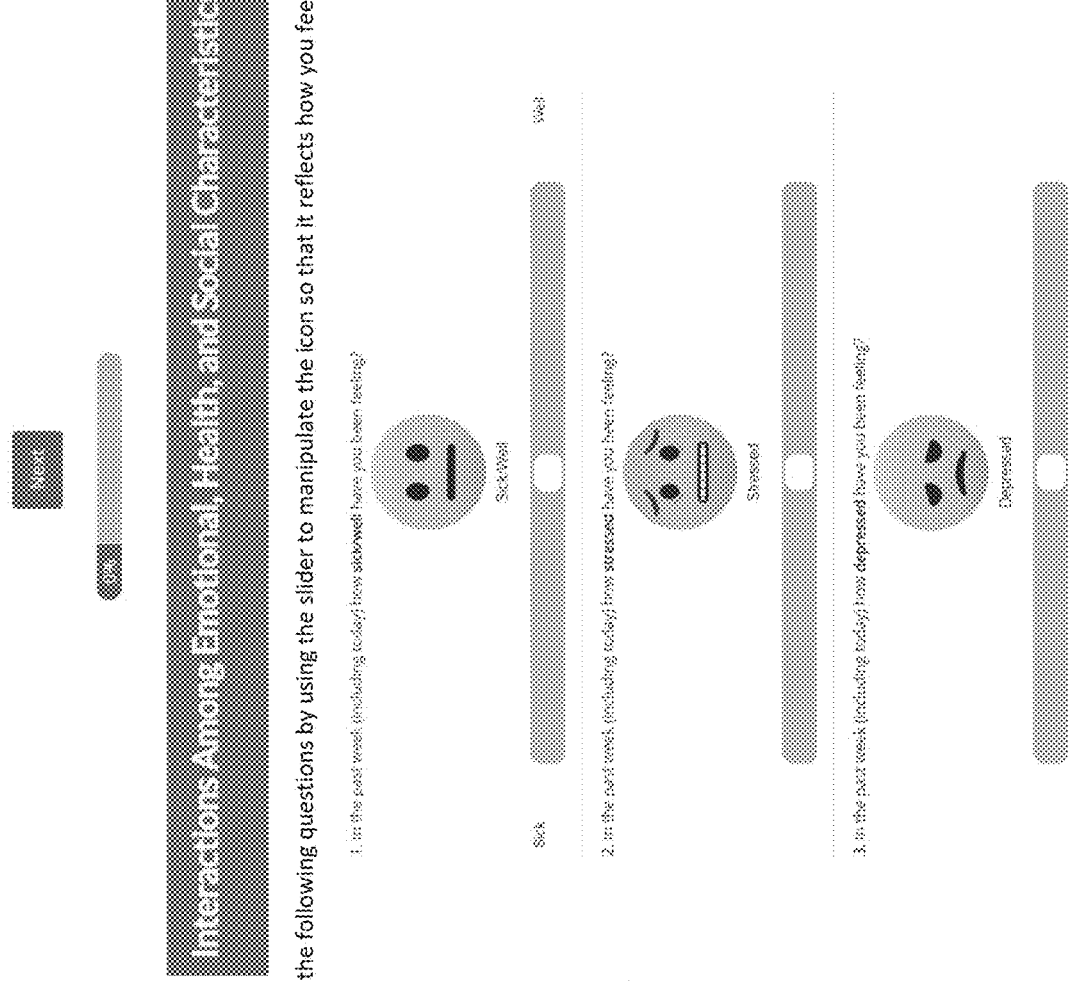
FIG. 2A is an overview of an introductory portion of an exemplary survey using graphical interfaces to capture and measure subjective experiences, for use in accordance with the present subject matter, and exemplary Emotional Characteristic components of the exemplary survey embodiment presently illustrated.
Figure 2B:
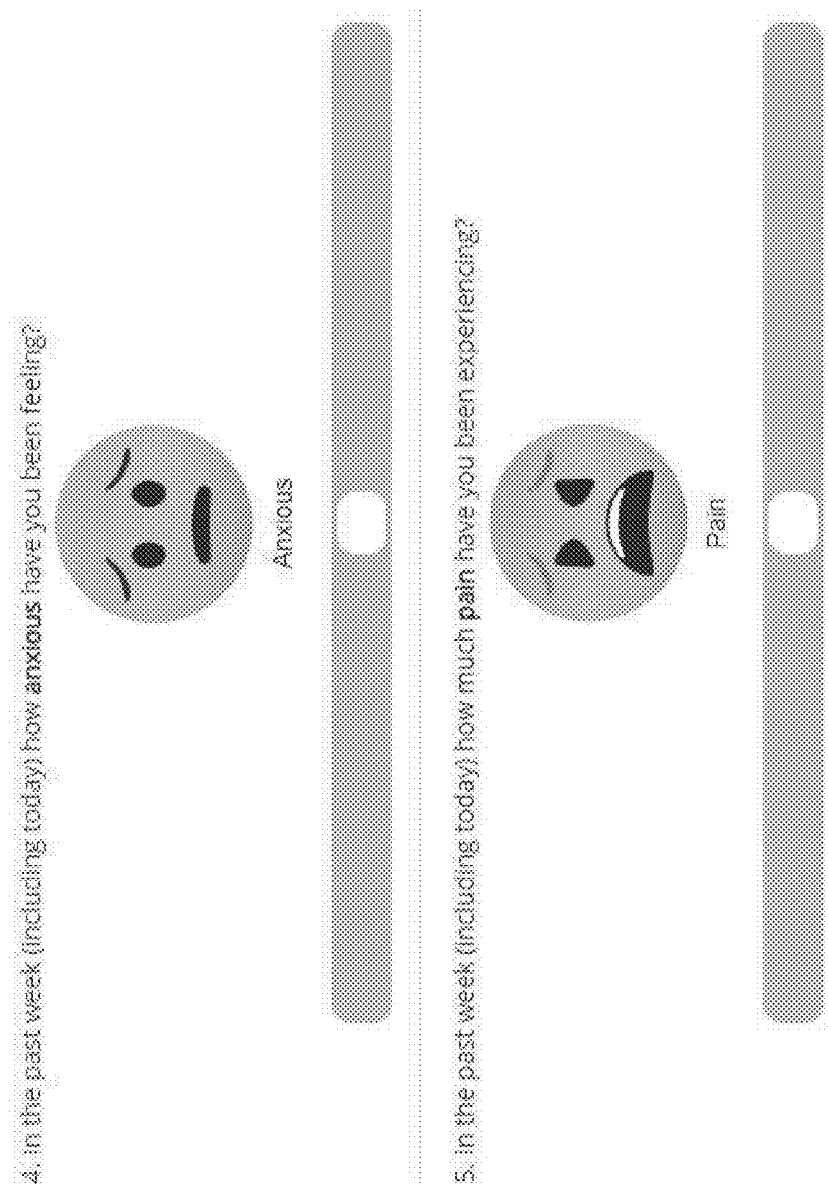
FIGS. 2B and 2C represent respective additional exemplary Emotional Characteristic components of the exemplary survey embodiment referenced per FIG. 2A.
Figure 2C:
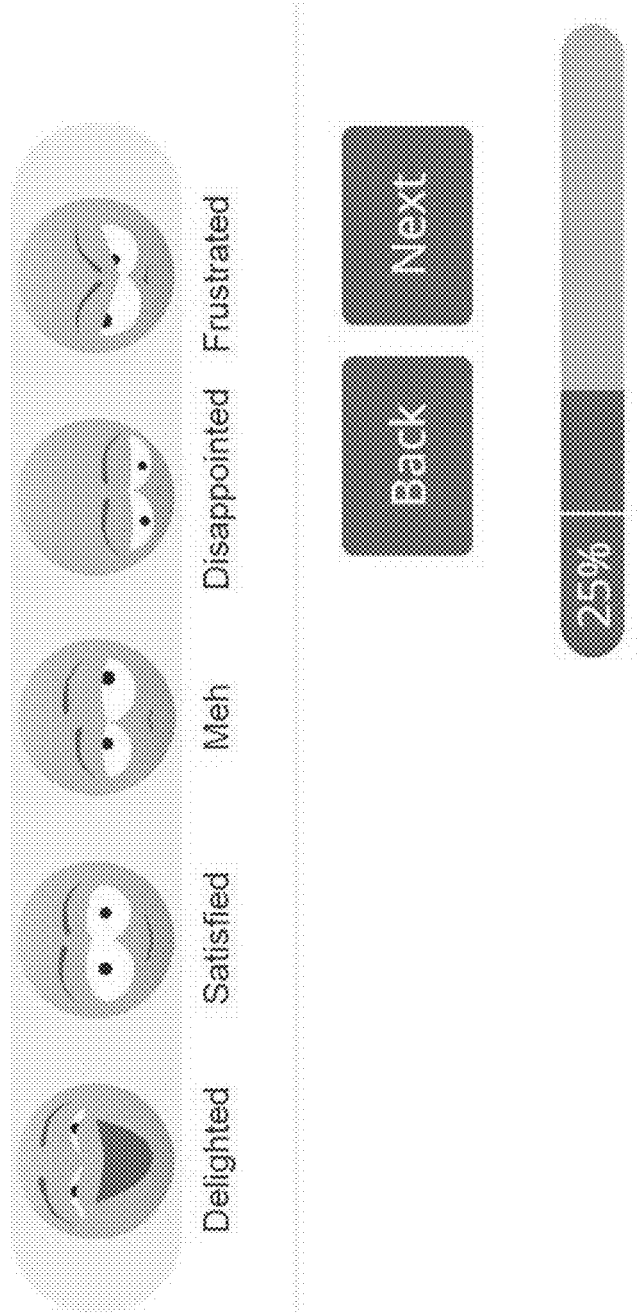
Figure 4A:
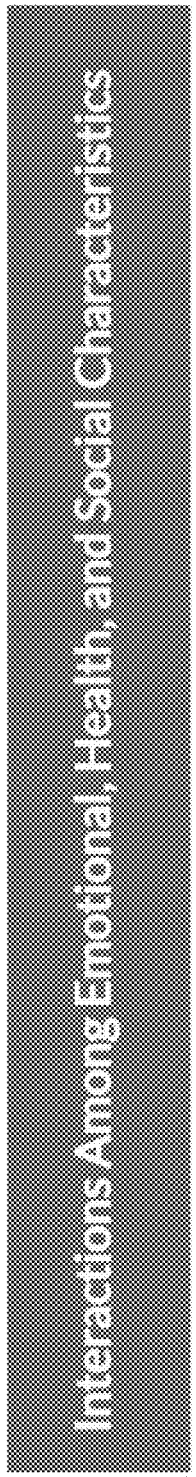
Figure 4H:
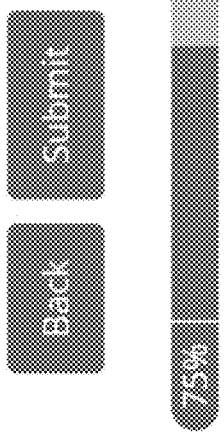

FIG. 2A is an overview of an introductory portion of an exemplary survey using graphical interfaces to capture and measure subjective experiences, for use in accordance with the presently disclosed subject matter, and exemplary emotional characteristic components of the exemplary survey embodiment presently illustrated. Participants respond to each question by using a movable bar to manipulate an icon so that it reflects how the respondent feels in response to each question, therefore capturing emotional/subjective information in definitive ways. FIGS. 2B and 2C represent additional exemplary emotional characteristic components of the exemplary survey embodiment referenced per FIG. 2A.

In more general terms, a graphical user interface (GUI) is a user interface that allows users to interact with electronic devices through graphical icons and/or sometimes audial cues, instead of using a text-based interface or navigation, or a typed command. In this instance, the actions in GUI's constituting transforming or shape-shifting icons, are performed through some form of user direct manipulation of graphical elements. With continuous representation, for example, of a range of images associated with a shape-shifting icon, direct manipulation by the user (such as a patient or other participant such as in a survey) provides immediate but reversible incremental actions and feedback through corresponding manipulation of the representing icon.

As GUI's are presently utilized per present disclosure, they help to achieve quantification of specific subjective experiences. One exemplary method for quantifying a subjective experience may include outputting an adjustable graphic that is continuously adjustable among multiple differing states. The position of an input device by a user may be manipulated to cause the adjustable graphic to be substantially simultaneously manipulated between differing states, resulting in an adjusted graphic. Whenever the involved graphics have been intentionally designed and validated for practical relationship to feedback regarding a particular topic, the user may match the adjustable graphic to their subjective experience regarding such particular topic. A scaled value or equivalent corresponding to the user-adjusted graphic may be calculated as a way to capture and definitively measure the user's subjective experiences for each of a plurality of survey questions, to form a set of data for the given user for the corresponding plurality of survey questions.

FIGS. 3A and 3B represent exemplary health characteristic components of the exemplary survey embodiment referenced per FIG. 2A. FIGS. 4A through 4H represent exemplary social characteristic components of the exemplary survey embodiment referenced per FIG. 2A. In some instances, such intelligence may be already known as background on a particular patient so that not all questions of the survey approach have to be addressed in each iteration of an assessment.

Figure 5A:
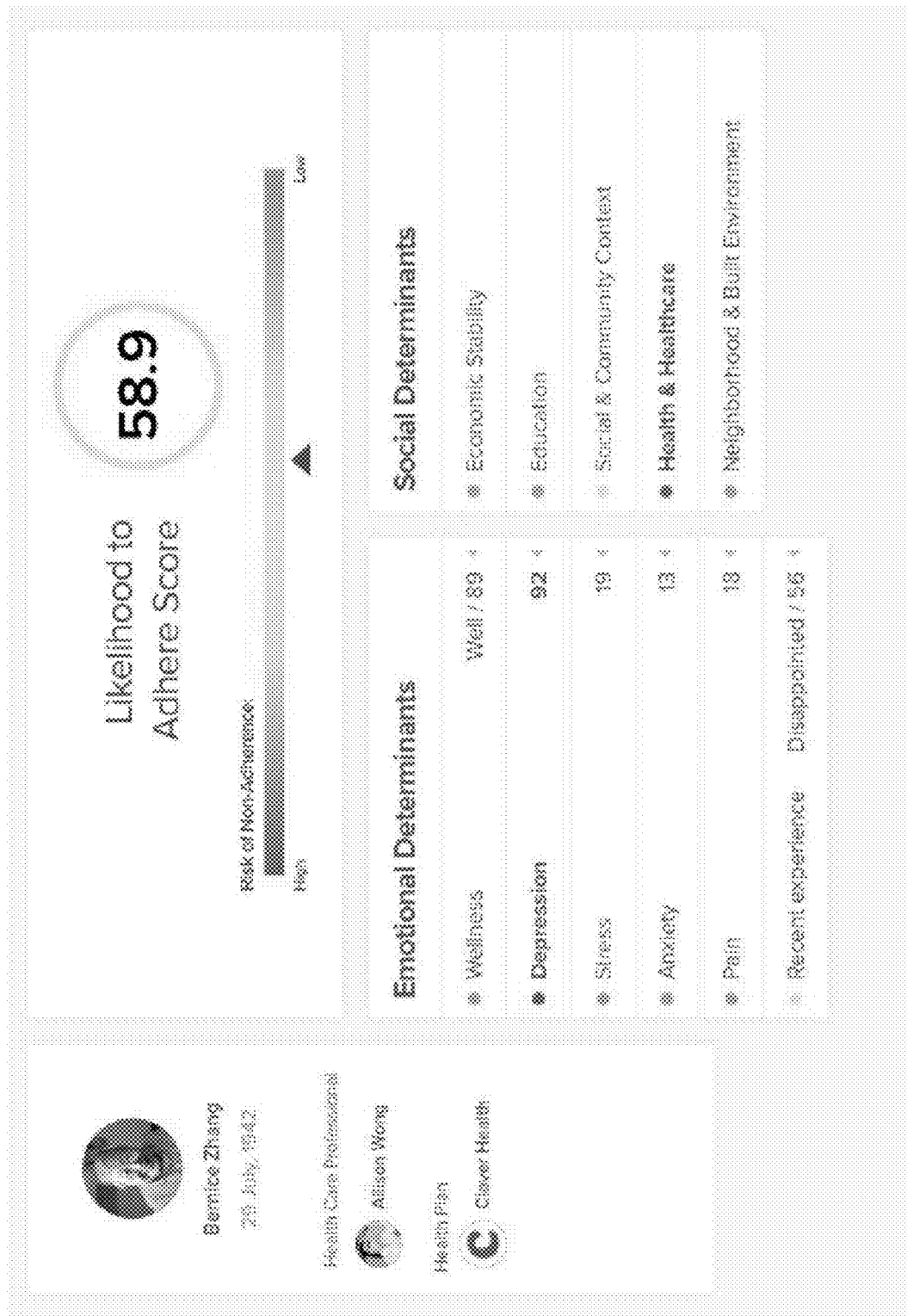
FIGS. 5A and 5B provide respective images of exemplary screen mockups of how presently discussed data could be captured and reported, using fictitious information and hypothetical responses for the example.
Figure 5B:
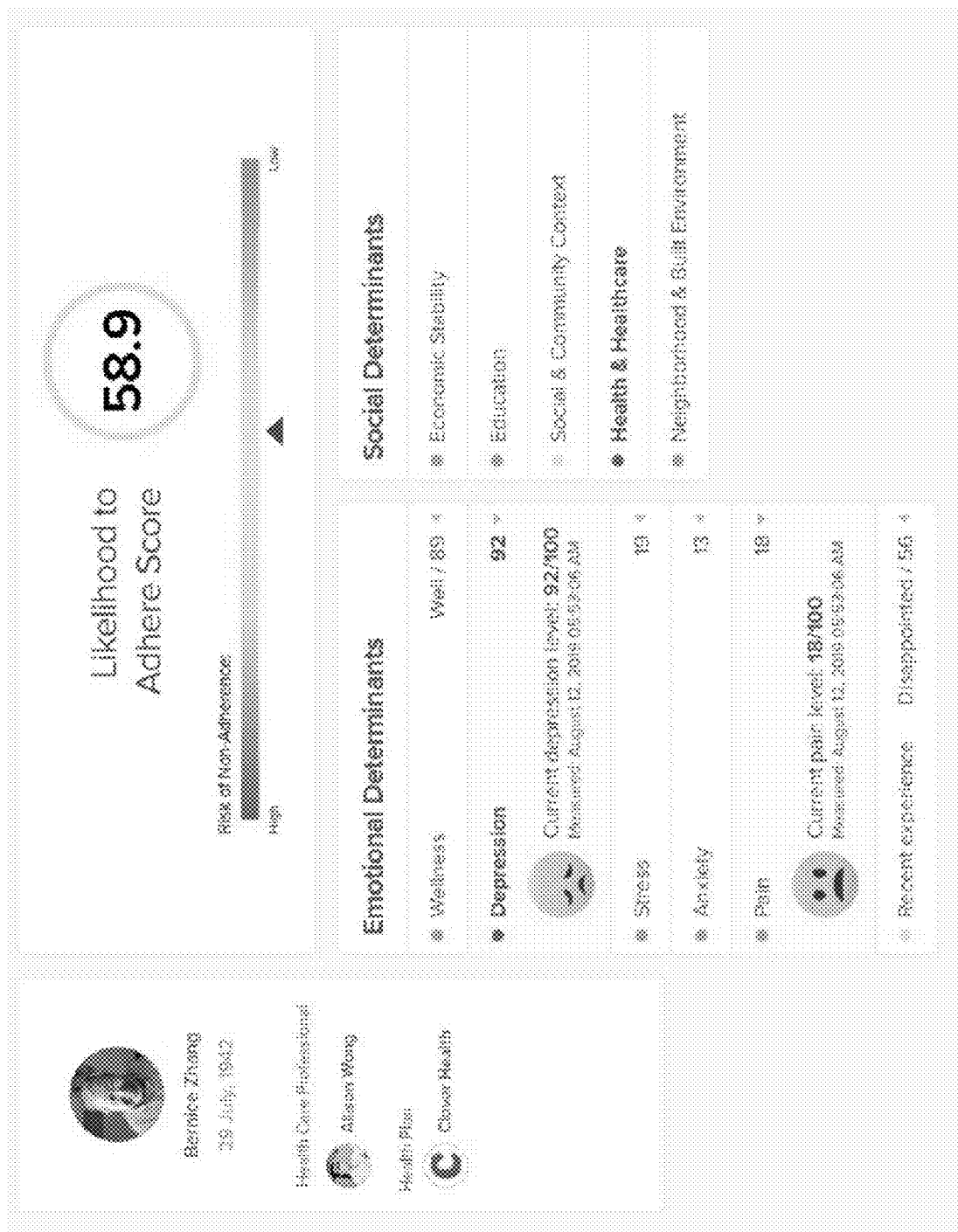

FIGS. 5A and 5B provide an exemplary mockup of how such information could be captured and reported using fictitious information and hypothetical responses for the example. FIG. 5B shows additional embedded information which may be provided by clicking onto drop-down menus, as shown in conjunction with scoring on emotional determinant examples for categories of depression and pain. Again, all example information and/or data throughout this specification is entirely fictitious and only for purposes illustration and example.

Use of emotional determinants for determining likelihood of adherence per presently disclosed subject matter provides a resultant score which may be termed as an Obstacles to Adherence (OTA) score or Likelihood To Adhere (LTA) score, or similar, which for example could be color coded as shown in exemplary FIG. 5C.

Platform for Assessment and Intervention Research (PAIR): System Design Document FIGS. 6-9 are referenced in conjunction with disclosure herewith which specifies architecture and system design of the Platform for Assessment and Intervention Research (hereinafter also "PAIR"). It includes a high-level architecture view of the platform and a high-level system design that include the basic data flows, the types of data collected, tracked, analyzed, and reported, and initial product results.

Goals & Assumptions
1. Define the Platform high-level Architecture and cloud model.
2. Define the Platform high-level system design and cloud model.

3. Define the Platform basic data flows, including the input data specifications, types and sources of data collected.
4. Define the Platform data that is tracked, analyzed and reported.
5. Define the Platform system design features that support data acquisition, analyses, and reporting to the health care providers.
6. Demonstrate the Platform foundational assumption that Use (i.e. data generation and platform-guided learning) may be achieved only by effectively combining high Usability (e.g. ease of use, minimization of workflow disruption, high user satisfaction) and high Utility (e.g. value returned to the user).
7. Demonstrate the assumption that usage of the Platform may support three foundational goals:
    A. Reduced cost of healthcare for mental health, acute health, and chronic disease prevention and management
    B. Improved outcomes in health improvement, maintenance, and management
    C. Improved patient and provider satisfaction in the delivery and consumption of healthcare services Platform Architecture Cloud computing is the primary architecture style of the Platform. At a high level, the cloud computing architecture style offers three main benefits to the Platform:
1. A highly scalable file and database system (aka storage and relational database) capable of high performance/throughput, supporting structured and unstructured storage (file and database) of large amounts of data, and capable of handling hardware failures without loss of data.
2. A highly scalable pool of compute resources which can be dynamically used to service a large number of simultaneous requests (e.g., ingesting multiple files), as well as marshaled together to parallelize a larger processing task (e.g., machine learning, processing an analytic).
3. A policy-based management service which assures the most efficient usage of #1 and #2, under various usage scenarios (end user synchronous, batch asynchronous) and security models.

Figure 6:
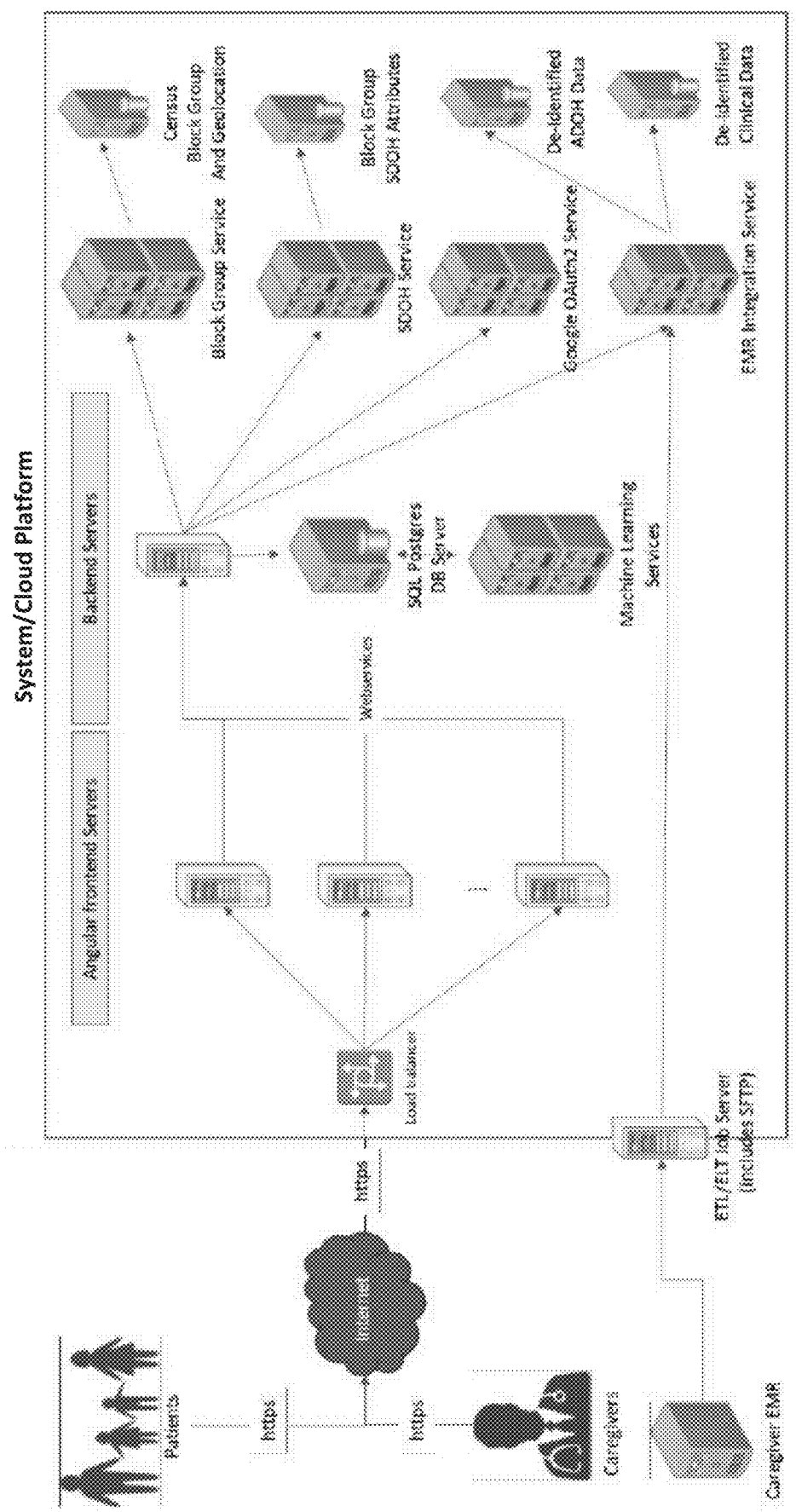
FIG. 6 illustrates a schematic of an exemplary embodiment of the presently disclosed subject matter Platform high level architecture, including the database (SQL Postgres DB Server) and primary data, compute nodes (backend servers) and visualization nodes (Front End Servers)

An exemplary embodiment of the Platform cloud computing architecture may be based on the Google Cloud Platform (GCP). FIG. 6 illustrates a schematic of an exemplary embodiment of the presently disclosed subject matter Platform high level architecture, including the database (SQL Postgres DB Server) and primary data, compute nodes (backend servers) and visualization nodes (Front End Servers). The presently disclosed Platform subject matter ingests relevant patient demographic and diagnostic data from eligibility, Electronic Health Records (EHR), and billing systems, and processes the data for retrieval and display of patients pertaining to a given clinic-level user. These data include:
  a. Full name
  b. Full Address
  c. Date of Birth
  d. Gender
  e. Ethnicity
  f. Patient ID number
  g. Primary Healthcare Provider assignment
  h. Clinic/service location; and
  i. Diagnoses.

The extract, transform, load (ETL) data model is used with data lake implementations. As an alternative to ETL models, extract, load, transform (ELT) is a model for which the data is not transformed on entry to a data lake, but is stored in its original raw format. The presently disclosed Platform subject matter ETL/ELT process automates updating of those attributes referenced above from the EHR through SFPT (Secure File Transfer Program: a true SSH File Transfer Protocol client from the OpenSSH project) and supports most transfer and connection protocols.

The presently disclosed Platform subject matter ETL/ELT process further automates imports from Scheduling software, whether embedded within EHR or otherwise freestanding, relevant appointment data as follows:
  a) A given patient's scheduled appointment date and time
  b) Appointment status (kept, no-show, cancelled, rescheduled); and
  c) Updated appointment date and time in wake of reschedules, cancellations, or no-shows.

The process of the presently disclosed Platform supports updates to appointment scheduling to occur automatically, as these updates bear on timing of administration of pre-episode and post-episode self-report measures. The presently disclosed Platform provides administrative functions such as secure account login, password retrieval/resetting, and addition/deletion/modification of patients that have been entered into the system per above.

The presently disclosed Platform automatically distributes to patients via SMS, email, or both (or other forms of communication including those presently in existence or later established), an initial self-report measure including but not limited to feedback on the testing re affective factors/determinants, and such as briefly providing scalar feedback on potential obstacles to health management. The Platform is designed to collect data prior to a healthcare encounter, whether that encounter occurs in-person, on-site, via telehealth media, or via other mechanisms. Collection is triggered when the Platform detects that a given patient has made or been assigned an appointment for a healthcare episode. See also the self-explanatory schematic overview of FIG. 7, which gives details on interactions for some embodiments of the presently disclosed Platform system interview process for patients. Collectively, FIGS. 8A & 8B also represent self-explanatory information on data and process/methodology flow for such interview process represented overall by subject FIG. 7.

Figure 7:
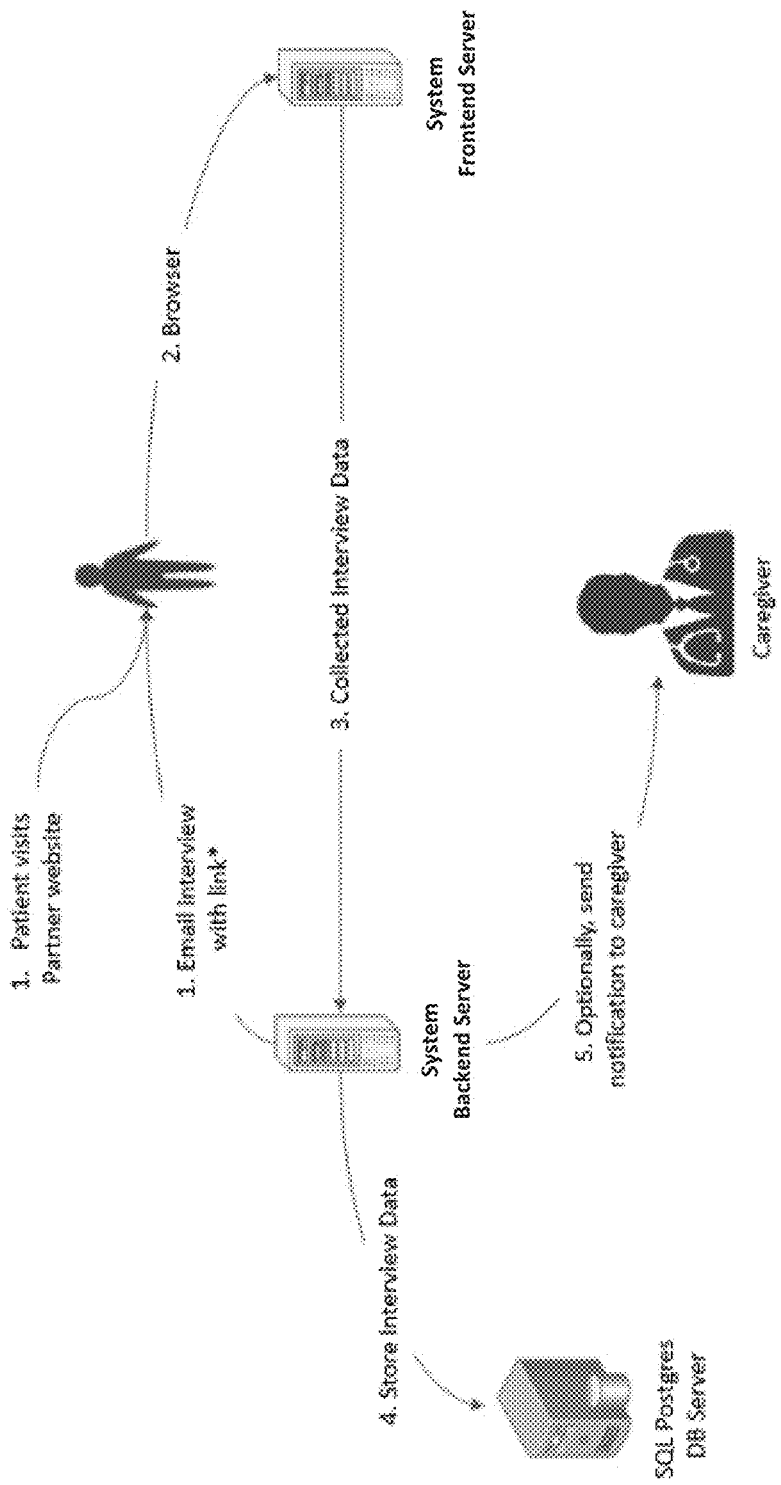
FIG. 7 is a self-explanatory schematic overview of details on interactions for some embodiments of the presently disclosed Platform system interview process for patients of FIG. 6.
Figure 8A:
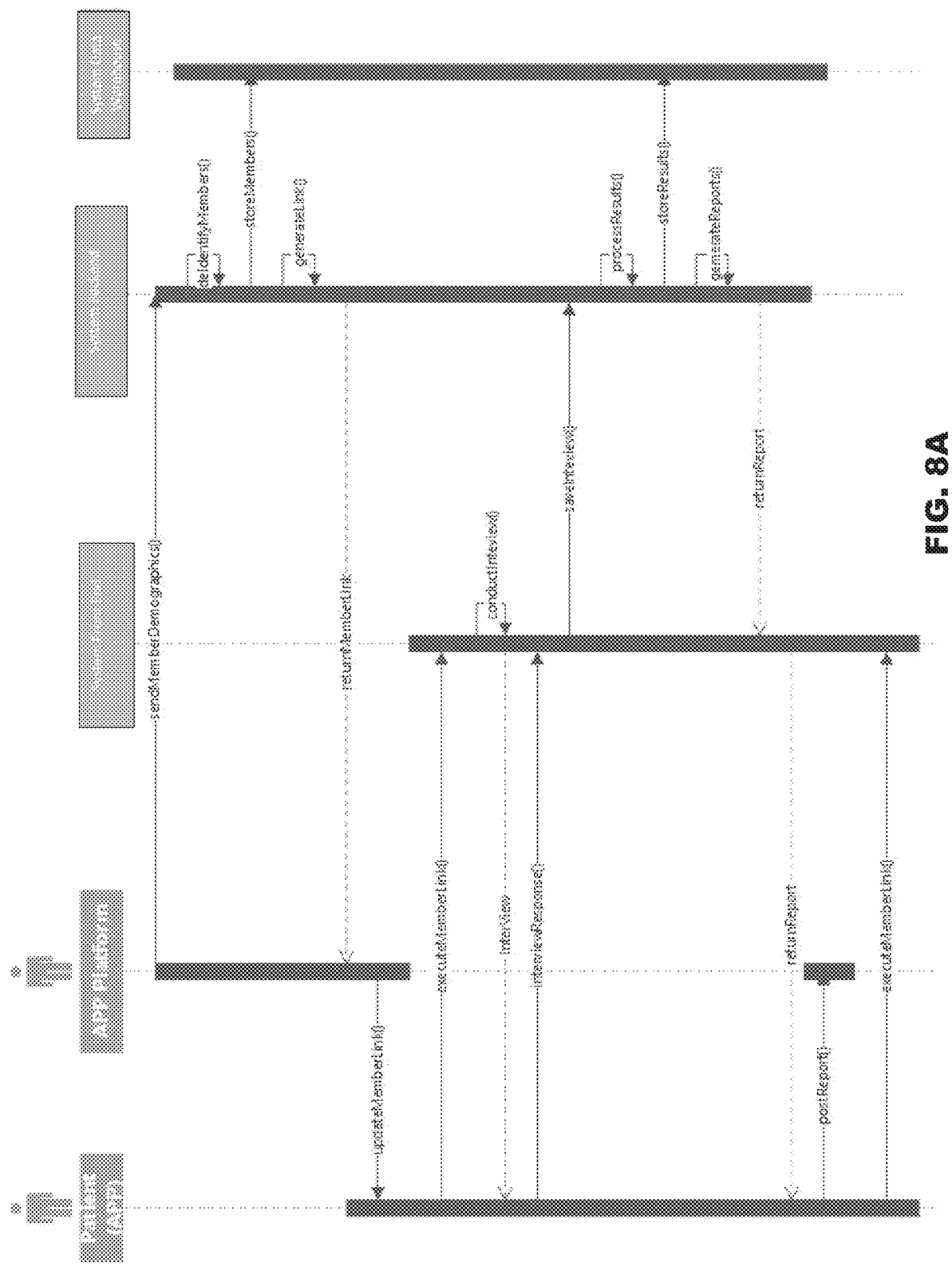
FIGS. 8A and 8B represent respective self-explanatory information on data and process/methodology flow for such interview process represented overall by subject FIG. 7.
Figure 8B:
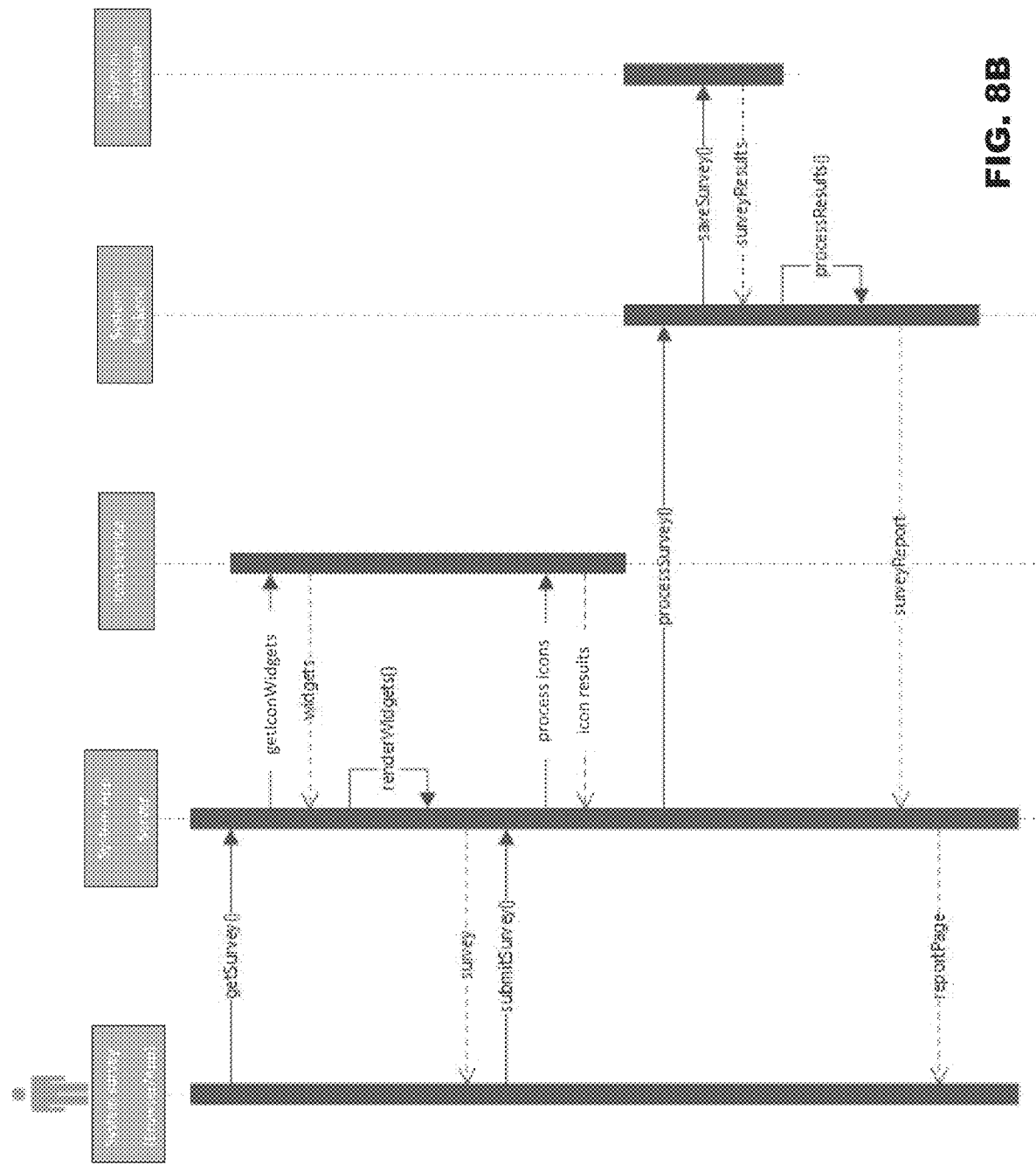

As illustrated and represented in part by FIGS. 7, 8A, and 8B, the presently disclosed Platform logic detects when the pre-appointment measures as defined above have not been completed within a configurable period of time and automatically re-distributes the instrument and records that it has done so, prior to a scheduled encounter.

Similarly, the presently disclosed Platform logic detects when the measures as defined in above have not been completed prior to patient arrival for the scheduled encounter. The subject Platform then alerts an administrative user (prototypically, a front office receptionist) to manually distribute the measure to the patient by email, SMS, or both. Should such distribution not be feasible, in the determination of that administrative user, the Platform supports distribution of the measure to an in-house device (e.g. tablet computer) so that the patient can complete it in the waiting room.

Figure 9:
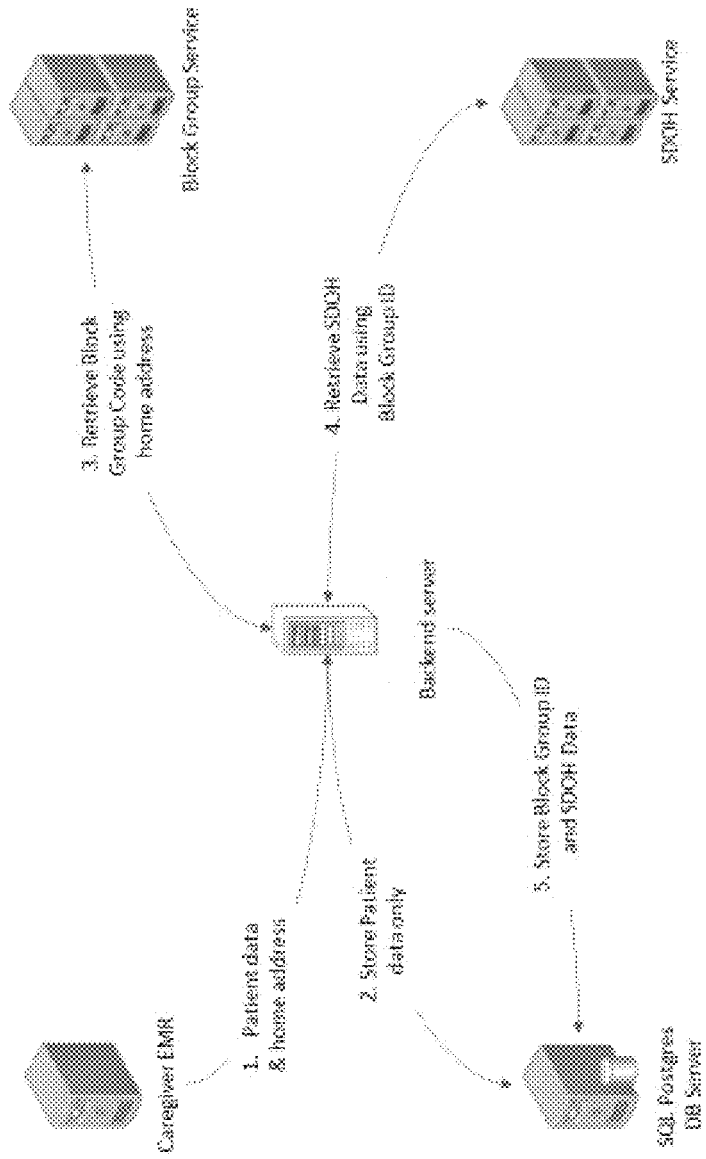
FIG. 9 discloses an overview schematic of presently disclosed process for retrieval of available social factor/determinant data in support of the presently disclosed Platform.

The presently disclosed Platform gathers and compiles intelligence on relevant social factors or determinants data about a given individual, at least (but not necessarily limited to) at the time that assessment or measure is taken of affective factors for a subject patient, or alternatively at the time the Platform detects that the patient has made or been assigned an appointment for a healthcare encounter. FIG. 9 discloses an overview schematic of such process for retrieval of available social factor/determinant data in support of the presently disclosed Platform.

The presently disclosed Platform supports identification of one or more sets of social and emotional factors or determinants, which separately and together (via a calculated Obstacles to Health Management/Maintenance [OHM] score) provide a metric designed to help predict likelihood of target outcomes, e.g. adherence to treatment plans, wellness activities, etc. for the individual from/about which such data have been gathered. The predictions as so enabled support identification of "drivers" in the form of affective and social factors, particularly those constituting obstacles to health management/maintenance, specific to the individual for which the OHM score is calculated.

Monitoring Process

The presently disclosed Platform may provide repeated administrations of self-report measures that reflect affective factors and potentially other factors, and track changes therein. The presently disclosed Platform may also provide for tracking changes in those drivers, as well as in the composite data scores across time, via repeat sampling of the individuals from which the requisite data may be gathered.

The presently disclosed Platform supports refinement of accuracy in predictive metrics across time within samples, populations, and within individuals across time, via System-internal calculations, which may be augmented by Machine Learning (ML). Via such functionality, the presently disclosed Platform supports learning what distinguishes people who occupy at least two or more strata of data-based scores (e.g. high, medium, and low for embodiments that use three strata, and based on relative comparisons). For example, the presently disclosed Platform provides knowledge that 68% of all persons in a High OHM score group within a given sample experience affective determinant Factor 1 at a significant level, whereas only 41% of persons in a Medium OHM score group within that sample experience that factor at that level.

The presently disclosed Platform supports repeated administrations of additional self-report measures (e.g., the Adherence Monitoring Survey) that can track affective determinants variables and/or additional factors, e.g. self-reported health management/maintenance-relevant factors including, but not necessarily limited to, obstacles to activities, activity levels achieved, motivation/intentionality toward higher levels of activity, etc.

The presently disclosed Platform supports for tracking of additional measures of adherence (e.g. BMI, blood A1c levels, billing/cost information, Rx fill/refill data, etc.) as inputs from providers or by other mechanisms. Such measures may represent outcomes, health status indicators, or other factors or phenomena.

Reporting

The presently disclosed Platform provides reports, intended for healthcare staff consumption, and possible others such as researchers, administrators, payors, or others, of an individual's calculated OHM score, the affective factors measured, the social factors measured, and the relative prominence (i.e. relevancy/salience) of those factors for individuals at given points in time, as well as other variables tracked across time. These may be aggregated for samples of patients, reported across time within a given patient, or both. These could take the form of reports of an individual's self-reported adherence levels, as well as relevant variables, such as the degree to which an individual feels he/she understands the treatment plan, his/her degree of intentionality/determination to improving his/her adherence levels, the relative degree of wellness or illness he/she feels, and the difficulties he/she has experienced in achieving full and consistent adherence. These may all be reported as averages of self-reports across time (e.g. recent 60 days preceding the most recent self-report). These difficulties may be focused in one or more major domains, including but not necessarily limited to: medication use, exercise, and nutrition.

Within such reporting functionality outlined above, trend analysis can be reported to indicate whether there have been (e.g. recent 60 days) changes for the better, for the worse, or no change.

Patient Support

The presently disclosed Platform provides access by patients to tools that can support increased activity, social support, guidance, etc. These could include one-touch access to information about disease states, relevant treatment plans details, nutritional information, self-care materials, one-touch access to live support via phone, video teleconferencing, SMS/IM chat; one-touch access to appointment scheduling resources, and more. These supports could be categorized at the database level as constituting Informational, Instrumental, Interpersonal, or other support types, and tracked as such.

The presently disclosed Platform allows for measurement and reporting of which support options outlined above have been utilized by a given patient, at what time(s), with what frequency, and for what duration. These data may contribute to revisions to the OHM score, or other scores, and tracked against changes in progress and outcomes.

The presently disclosed Platform provides reporting functions that can be viewed via computer terminals and/or laptops and tablets, by front-office personnel and by healthcare providers. These reports could be printable if desired.

To Healthcare Providers

By gathering such presently disclosed patient-based affective factor data, and by analyzing and reporting those data to providers in an easily-digestible, actionable form, the provider has increased knowledge of and insight into potential subjective, intrapersonal factors that could represent obstacles to health management/maintenance. By likewise gathering such presently disclosed patient-based social data that might otherwise be unavailable, and by analyzing and reporting those data to providers in an easily-digestible, actionable form, the provider has increased knowledge of and insight into potential circumstantial factors that could represent obstacles to health management.

The patient-based affective factors also concurrently serve to highlight patient experiences that themselves may represent targets of healthcare goals; namely, indicators of potential mental health disorders and dysfunctions, pain disorders, and stress-induced disorders. This could indicate the need for a more thorough assessment of loneliness, depression, anxiety, stress, pain, and overall subjective sense of wellness/illness and/or other affective factors. The patient-based affective factors can also include brief assessment of patient experiences regarding recent contact with the healthcare provider system (e.g. via in-person visits, via telephone contact, via website interaction, etc.) potentially useful for quality-assurance monitoring of patient satisfaction levels.

By compiling patient-based affective and social factors data, analyzing them, and reporting them to providers in an easily-digestible, actionable form (i.e. in a single score, normalized to some set range, such as ranging from 0 to 100) represented by the OHM score (and/or other scores), providers are able to see relative stratification of risk for non-adherence and consider different treatment plan modifications for persons occupying the different high, medium, and low adherence likelihood strata.

By providing repeated measures and assessments of such patient-driven data, providers could be able to monitor and track changes in these, as well as in the underlying contributing drivers thereof. By providing repeated self-reported measures of activity, affective and related factors, providers are able to see recent and historical data highlighting specific obstacles to social support, adherence, healthcare access, and other health maintenance/management activities. By providing for input (by providers) of other, non-self-report data (e.g. BMI, weight, A1c levels, etc.), providers are able to compare changes in those measures to self-reported data, and to examine disparities between self-report and objective data.

By providing information about incidents and frequencies of patients' usages of support mechanisms (e.g. download accesses to information; live conversations with in-house or third-party adherence coaching/support; patient-initiated healthcare episodes not otherwise previously scheduled), providers are able to see whether such support mechanism access has impacted OHM, actual adherence levels, related factors, and (when applicable) objective measures of adherence and/or outcomes.

By automating most all functions of data gathering, analysis, and reporting, including timing of pre-episode and post-episode self-report measures, trends, and feedback, providers are able to make more use of their time with patients (via increased knowledge and insight) while workload stress on front office personnel is minimized. Pre-episode and post-episode in the presently disclosed context refers for example to pre- and post-appointment or healthcare provider encounter, whether in-person or virtual/telephonic or via a cloud or internet-based system.

Patients who have need for clinical attention to such experiences as illness, loneliness, depression, anxiety, stress, pain, and consumer-dissatisfaction, and/or others can be more readily identified and interventions/remediative measures considered by their providers. By allowing providers more knowledge/insight about social factor variables that might otherwise go unreported and even unasked, patients' social circumstances can be taken into account in understanding their overall obstacles to better health.

To Patients

By allowing patients to self-report on such subjective affective factors as loneliness, depression, anxiety, stress, pain, wellness/illness sensations, and feelings engendered by recent encounters with healthcare providers (or their representatives), patients are given a greater voice in their healthcare interactions. Thus, patients who have clinical needs for attention to such experiences as illness, loneliness, depression, anxiety, stress, pain, and consumer-dissatisfaction, and/or others can be more readily identified and interventions/remediative measures considered by their providers.

By allowing providers more knowledge/insight about social factor variables that might otherwise go unreported and even unasked, patients' circumstantial considerations can be taken into account in understanding their needs.

By allowing patients to self-report regarding their temporal experiences of affective factors, adherence levels, their sense of how well they understand the nature and requirements of their treatment plans, their determination regarding improving their adherence across time, and the obstacles they may encounter (internally and externally) in their efforts to manage/maintain their health consistently, patients' insights into their own circumstances, considerations, and patterns can be heightened. This can increase their sense of engagement with healthcare providers and with the processes of prevention/treatment of chronic healthcare conditions. This can support greater self-advocacy on their parts.

By allowing patients access to support mechanisms (e.g. web-based information, live interactive support, and ready-access scheduling of new appointments), patients can take more active parts in their own self-management and potentially benefit from those supports.

To Payors

By increasing patient engagement, providing access to support interventions that can increase health management/maintenance activities and patient satisfaction, and by increasing the capacity for providers to predict, monitor, and intervene in variables pertaining to adherence, clinical outcomes may be improved, resulting in diminished mortality, morbidity, and costs.

By increasing the capacity for payors to predict and monitor patients' health management/maintenance, they may be able to reward performance by providers and their systems more effectively.

By providing the basis for a marketplace environment (e.g. allowing different adherence coaching service providers to compete for opportunities for incorporation in the presently disclosed Platform), the resulting system may allow for greater cost savings via increased competition.

The following portion of disclosure relates more directly to creation and validation of shape-shifting icons per presently disclosed subject matter for use in presently disclosed methodologies.

Shape-shifting icons are selected as part of practicing the presently disclosed Platform, and then adjusted by end users to represent specific types and intensities of subjective experiences, yielding scalable, quantified data in the form of numeric values of nominal, ordinal, interval and ratio types for storage, reporting, and analysis. The graphical user interfaces (GUI's) can be supplemented by a visible, adjustable scroll/slide allowing an end user to adjust the visible nature of the display characteristics, but in some iterations no scroll/slide is visible (e.g. as in adjustment via touch-sensitive devices or by other input methods). Similarly, in some iterations specific names or labels for the shape-shifting icons appear to aid identification, differentiation, and selection by an end user, whereas in other iterations the configuration of graphical elements alone, potentially in combination with variations of color, overall form, or other characteristics, can serve those purposes. And, in some iterations, numeric values may be displayed to represent the degree of change in the image from one endpoint to another, or to represent other characteristics of the transformable object image, such as the degree at which within a range a given configuration is situated.

Operationally, users select specific shape-shifting icons to represent a subjective experience they wish to identify as one that they are currently experiencing, that they recall from the past, that they envision as potentially occurring in the future, or that they believe represents a current, past, or future subjective state experienced by another person, another living entity, or even non-living entities (e.g. cartoon characters). They then adjust the apparent intensity of the affect display to fine-tune the degree of the experience, perhaps between a neutral (absent) degree and an extreme degree of intensity, or between two polarities, or among variations in a two- or three-dimensional representation of alternatives. They may do so, as noted above, via visible selectors, touch-sensitive input methods, or other methods, for example, such as with movement or spoken/sound responsive systems.

The graphical displays stimulate subjective experiences of familiarity to the degree they resemble, or fail to resemble, specific states of experience, via what we refer to as resonance, which we believe to be related to experiences of mirroring, familiar to us from attachment theory. The experience of resonance (familiarity) to greater and lesser degrees, is understood theoretically via the operations of visual perception system(s) for color, shape, movement, contrast, discrimination, etc., along with memory systems (recognition, recall; explicit, implicit; episodic, semantic; etc.), and imaginal systems. Theoretically, these are predicated upon theory of mind operations and empathy, possibly via invocation of a mirror neuron system.

The transforming icon technology Platform stores and reports in real-time, self-report data representing the type of experience selected and the intensity registered, without requiring users to try to quantify their own degree of how much they feel a given subjective state, as is otherwise the case with known systems such as Likert response type scales and 5-star rating systems. Furthermore, such other known scales or systems are what are referred to as discrete format visual analog scales, as they yield only discrete, as opposed to continuous data. The transforming icon technology Platform yields truly continuous data, and are thus an example of continuous format visual analog scales. Inasmuch as the intervals between any two iterations of a transforming icon produced by the scale builder are quantified and known, the resulting data are of interval/ratio type, making parametric analyses of data possible.

Additionally, because they are standardized across applications and other platforms in which they are embedded, shape-shifting icons avoid the chaos inherent in emojis, which are not consistently labeled with any specific emotion type identifiers, are not modifiable for intensity, are not constructed upon any consistent underlying theory of emotion, or even consistently rendered across one operating system to another. Anthropomorphic emojis aren't designed to convey specific feelings so much as they're designed to conform to instructions as to what the facial features should look like. In fact, emojis are very easily misinterpreted even when used and displayed between devices within one operating system.

Furthermore, transforming icon technology is more clear as a method for representing specific types and intensities of subjective experiences than are text analytics technologies—commonly referred to as text-scraping—which are fraught with error when it comes to identifying specific feelings, and particularly their intensities. Because shape-shifting icons allow direct self-report of subjective experiences with respect to type (e.g. anger) and intensity, the presently discussed transforming icon technology Platform generates direct data rather than inferential data.

Finally, transforming icons are different in that their very nature is novel and unique, inasmuch as they offer the user the opportunity to "see" a depiction that most closely approximates and represents his/her subjective experience, offering a more direct (i.e. less analogue, if you will) opportunity for communication of otherwise difficult-to-quantify internal states and experiences. All other visual analogue scale types require a user to, in essence, quantify his/her internal state, experience, memory thereof, or imagining thereof (as in hypothetical situations).

What Sort of Data are Produced?

The transforming icon technology Platform stores and makes available for reporting numerical values representing the GUI images themselves (along with their labels, if such are used). These are reportable as nominal data. The Platform also stores and makes available for reporting the shape-shifting icons' identified modifiable elements' data points (e.g. those corresponding to the eye whites, the mouth, an eyebrow, etc.), the position of all such modifiable elements' data points along the interpolated pathways, and metadata pertaining to use instances.

In practical terms, a "happy" transforming icon might be identified as a nominal data point, $x=1$, while variations of a transforming icon's display along a continuum might be stored as interval or ratio data $y=$[within range 0.00 to 100.0]. Associated metadata may take any of several forms, including nominal, ordinal, and interval/ratio and combinations thereof.

How are Shape-Shifting or Transforming Icons Created?

Individual transforming icons are designed and rendered via software, which we nominally refer to as the transforming icon Scale Builder. This system uses suitable digital images and interpolates a continuum of display modifications between those images. The result is a single display, the characteristics of which are modifiable by means of some input method (e.g. manipulation of a selector on a scroll or slide), such that the apparent image transforms or shape-shifts from one state to another through a continuum of change in the size, shape, position number, color and/or other characteristics of the elements of the display. That singular display can portray any of the suitable images entered into the system, as well as a practically infinite range of interpolated variations thereof, including extensions of the size, shape, position, number, color or other characteristics of the elements of the display beyond the boundaries otherwise delimited by the original entered images. Practically speaking, the system can render a practically infinite range of images that can be interpreted as more, or less, representative of a given construct they are designed to represent.

As an example, consider the entry of two anthropomorphic emoji, one representing what appears to be a happy facial expression and another of which representing what appears to be a neutral facial expression, into the Scale Builder. Upon execution, the system renders a single image that can be adjusted via a scroll or slide selector position at the far left of an apparent range, at which point the display is identical to the "neutral" image. When a user moves the selector to its extreme right-most position, the display is identical to the "happy" image. At intermediate points on the scroll or slide, depending upon the position of a selector, controlled by the user, the display could portray some interpolated image representing a point consistent with the distance of the selector from either extreme, and thus the variation between "neutral" and "happy" that the system defines as the corresponding distance along a variety of 1:1 pathways between data points in the "neutral" image and the "happy" image.

How are Shape-Shifting or Transforming Icons Validated?

Shape-shifting icons represent a new and novel method for capturing and reporting data pertaining to subjective experiences, and are comprised of several elements in their construction, display and use (e.g. size, color, shape, opacity, data input methods). As such, shape-shifting icons operate under several psychometric assumptions, including prominently the assumption that they are validly useful for the tasks they are designed to aid. In fact, it is part of the presently disclosed subject matter that shape-shifting icons are in fact more valid for the capture and reporting of data pertaining to subjective experiences than are other extant methods. Furthermore, shape-shifting icons are intended to be more engaging to users than alternative methods purporting to capture and measure subjective experiences.

Therefore, shape-shifting icons operate on two primary assumptions, which give rise to empirically-testable hypotheses:

Assumption 1: shape-shifting icons are a valid method for people to report subjective experience types and intensities thereof; and Assumption 2: shape-shifting icons an engaging method for people to report subjective experiences types and intensities thereof.

Research as presently disclosed can be performed to support the creation, deployment, evolution, and use of shape-shifting icons, with particular emphasis upon creating tools (as each transforming icon GUI is, indeed, a tool) that are validly useful and engagingly used. What follows is one example of an organic outline of activities reflecting formal investigation into basic psychometric properties of the UI's, which may be supplemented across time by naturalistic observations of transforming icon usage gleaned in coordination with external entities (e.g. potential customers, actual customers, other collaborators) who help us to investigate use cases for this new technology.

Validation Program
I. Shape-Shifting Icon Validation Initiative
  A. Face Validity Initiatives
    1. Forced-Choice Validation Engine Paradigm
      a. Core shape-shifting Icon validation studies
      b. Insights shape-shifting Icon validation studies
      c. Roseman shape-shifting Icon validation studies
      d. Healthcare shape-shifting Icon validation studies
      e. Mood shape-shifting Icon set validation studies
    2. Intensity Rating Validation Paradigm
      a. (Do people rate the 1.0 expressions as 10/10?)
      b. (do people rate the 0.2 expressions as 2/10? Or, alternatively as 1/5 the rating they gave to the 1.0 expression?)
  B. Scale Validity Initiatives Such Validation Program outline can be better understood by explanations of each layer. Neither the outline nor these elaborations are intended to be considered fixed and unmodifiable, as new initiatives, data, and priorities may result in modifications to the structure of the outline and/or to the elements therein.

Layer I represents a high-level initiative, Validation of Shape-shifting icons, reflecting efforts to test Assumption 1 as listed above. Specifically, this initiative investigates the individual shape-shifting icons that are the user-interface graphics referred to herein as transformable or shape-shiftable objects, and the scaled values that are derived from them, for evidence of various forms of validity. This could in some instances be contrasted with other major initiatives, such as Investigations into User Engagement, which might be labeled as II in such an outline.

Layer I.A., Face Validity Initiatives, represent one strategic direction within the Validation of Shape-shifting icons initiative, aimed at helping to establish evidence of one form of validation, focused on face validity. Setting aside the ironic fact that we're focused on transformable objects that are for the most part constructed to resemble human faces, face validity is a form of construct validity, which essentially poses the question, "Are we measuring what we intend to measure?"

Briefly, what we intend to measure are subjective human experiences that can presumably be represented by visual stimuli and/or text labels. Establishment of face validity serves that goal by testing "the extent to which a test is subjectively viewed as covering the concept it purports to measure. It refers to the transparency or relevance of a test as it appears to test participants."

Layer I.A.1., Forced-Choice Validation Engine Paradigm, refers to one tactic used in pursuit of evidence for and/or against the face validity of the shape-shifting icons. In this method, one may use a Forced-Choice Validation Engine which is a purpose-built online surveying tool for investigations. The Engine presents two variations of shape-shifting icons, at least one of which is designed to represent a target construct (e.g. the feeling of sadness), and which forces a response from a test subject as to which of the two images, if either, appears to them to represent the target construct. We determine which of the presented images is the correct response, reflecting our hypothesis that we have created a transforming icon that presents images representing a specific construct, and not representing other relevant competing constructs. These images are not themselves labeled; instead, essentially the subjects are asked to label them by a process of elimination.

In the Engine paradigm, while facing two images, one of which we presume to reflect a target construct of interest, people must choose which of the two images (if indeed either seems to) reflects the construct of interest, which is offered to them in the form of a question, "Which of these looks_____?" where the blank is filled in each trial with the name of the construct (e.g. Anger) being tested in that trial.

When people choose a transforming icon image as the "correct" one in a given trial, and the chosen one is NOT the one designed to capture the target construct, this is considered a false-positive selection of the chosen image, and is considered evidence that the transforming icon constructed to represent the target construct does not perform as well as the option against which it failed to compete. When people declare that neither of the two transforming icon images displayed in the Validation Engine's forced-choice paradigm represents the target construct, we say that we have evidence that the transforming icon designed to represent the target construct has failed to represent the construct and does not seem to represent the foil construct, either, resulting in an inference that the target transforming icon is not representative of the construct. Data are generated as simple counts and as percentages.

Layer I.A.1.a., Core transforming icon technology Validation studies, represents those surveys conducted with a particular set or subset of shape-shifting icons (in this case, all or some of the six shape-shifting icons designed to capture the constructs of sadness, anger, joy, fear, surprise, and disgust) and the data that come from those studies. These data provide evidence for and/or against the face validity of each of the specific shape-shifting icons within this set that are tested. These data typically represent successive efforts to produce transformable objects that are perceived—literally at face value—as representing the constructs we intend them to, and NOT representing constructs we do NOT intend them to (i.e., evidence of discriminant validity, within the context of construct validity). Other validation runs pertain to other sets and subsets of shape-shifting icons, e.g. Healthcare shape-shifting icons and Roseman-model-based shape-shifting icons, which could be labeled I.A.1.b. and I.A.1.c, respectfully.

A Working Model for Investigation and Success Criteria

Given the outline of proposed activities outlined above, we have undertaken what we have determined to be the most important early work that must be pursued: evidence for and/or against construct validity of shape-shifting icons. In so doing, we have established a working model for demonstration of face validity with a forced-choice paradigm. This working model is intended to allow us to take a series of iterative steps toward greater, defensible confidence that we have built transformable objects that accurately represent the constructs we intend them to, and that do not represent other competing constructs. This model is designed to provide increasingly stringent tests of validity, which we refer to as levels of confidence.

Level One: This is the most liberal level of evidence to defend our aspirational intention statement, "We have designed tools that measure the human subjective experiences we intend them to."

Practically and strategically, using data generated by our Forced-Choice Validation Engine, at this level we are able to say for any given transforming icon, "We tested a U.S. sample of not less than 100 persons ages 16-65 years of mixed genders, ethnicities, ages, and geographical locations, and found that they saw each image as representing the construct we intend it to represent, with a low degree of confusion as to the image's representation of other constructs instead." This means that we have applied an analogue to the Reasonable Person Standard in law, and we make no further claims as to the specificity or generalizability of the findings with respect to subsets of the sample or others in the population(s) sampled.

Objectively speaking, we have elected to define this operationally as given a transforming icon image representing what we consider to be an very high-intensity display of facial features denoting a target emotion, a reasonable sample of U.S. persons will agree in 90% or more of trials against at least five alternative foils designed to represent other constructs instead, that the transforming icon image does represent the target emotion and not one of the alternatives putatively represented by the foils. We chose 90% as a minimal criterion in order to suggest that in the vast majority of cases, viewers will recognize and utilize a given transforming icon as a visibly-evident representation of a subjective experience.

Furthermore, similarly and critically, at Level One we also endeavor to establish minimal evidence that we have created not simply static images to represent those subjective experience constructs, but also scaled values that are at least ordinal in nature and, aspirationally, interval and even ratio in nature, to represent degrees of the target construct. This reflects the hypothesis that the construct is experienced along a continuum commonly referred to as intensity. We do this at Level One by testing lesser-intensity images rendered by the presently referenced Scale Builder to see if they are perceived as representing a given target construct. We use a lesser criterion level of 50% correct identification, contrasted with the 90% criterion applied to the highest-intensity image of the transforming icon designed to capture that construct, because they represent less extreme variations away from a neutral, non-expressive configuration of facial features.

Thus far, we have chosen images that represent a point 20% along the continuum of images rendered from a uniform Neutral Face by our Scale Builder to test, as this also is the current "resting point" of expressiveness we use in working versions of shape-shifting icons in the applied field. We have done this with the rationale that even low-intensity representations of the target construct should be generally agreed-upon as accurate.

Operationally, then, with respect to evidence for a scale of intensity along a continuum, we state this as follows: Given a transforming icon image representing what we consider to be a low-intensity display of facial features denoting a target emotion, a reasonable sample of persons will agree in 50% or more of trials against at least five alternative foils designed to represent other constructs instead, that the transforming icon image does represent the target emotion and not one of the alternatives putatively represented by the foils.

Level Two: The aim in Level Two is to apply tighter controls over error rates. A more defensible statement can be made when the characteristics of a max-intensity transforming icon that meet Level One criteria also result in there being no foil image from another transforming icon accounts for more than 5% of the total trials as false-positives (i.e. that no other transforming icon image is considered a better representation of the target construct in more than 5% of the trials) when there are five or more alternative shape-shifting icons competing with the one designed to represent the target construct, and no foil image from another transforming icon account for more than 10% of trials being considered "neither" by subjects in a given study. In other words, no other transforming icon leads people to say that neither the foil nor the constructed transforming icon for that target construct represents it well. By extension, we seek at Level Two evidence that the lesser-intensity images passing Level One criteria additionally are found to have no other transforming icon images (foils) in that study accounting for more than 15% of the total trials as false-positives, and no other transforming icon images (foils) accounting for more than 30% of the trials being considered "neither" by subjects in that study. At this level, still the Reasonable Person Standard is applied for sample selection and with respect to specificity and generalizability.

Level Three: The aim in Level Three is to further tighten the controls over error rates, by requiring that max-intensity images be correctly identified (against not less than 5 alternative constructs) in at least 97.5% of trials in a given study, and by requiring that lesser-intensity images be correctly identified (against not less than 5 alternative constructs) in at least 80% of trials in a given study. At this level, still the Reasonable Person Standard is applied for sample selection and with respect to specificity and generalizability.

Level Four: In Level Four, the aim is to establish that the criteria met in Levels One, Two, and Three are adequate for various U.S. sub-populations, by examining the shape-shifting icons passing those criteria in more controlled samples. For example, we could investigate whether and to what degree the shape-shifting icons retained through Levels One, Two, and Three perform well with persons identifying as male, female, or other gender identities. As another example, we could investigate whether and to what degree those shape-shifting icons perform well with persons of various racial/ethnic identities. As still another example, we could investigate whether and to what degree those shape-shifting icons perform well with persons of various age groups. And, we could investigate whether and to what degree there are interactions among such variables. For example, we might find that a given transforming icon performs well with highly heterogeneous samples for those three variables, but poorly within a subset of African-American women between the ages of 16 and 24 years of age.

Level Five: The aim of Level Five investigations is to extend our explorations to persons of non-U.S. residence or origin, particularly with respect to those for whom English is not a primary language.

Core Transforming icon Set Validation: Design, Results, and Data

Employing the Forced-Choice Validation Engine paradigm, we sought to establish Level 1 face validity for each of the six shape-shifting icons (Sadness, Anger, Happiness, Fear, Surprise and Disgust) collectively referred to as Core Shape-shifting icons. For these trials, each transforming icon was identical in size, shape, color, number/configuration of elements designed to resemble human eye whites, pupils, eyebrows, and mouths, and the baseline Neutral image representing the lowest-intensity value (0.0 on a scale of 0.0 through 1.0) of each construct investigated. What was left then to vary was the shape, location, and sizes of the facial elements as they transformed from the Neutral expression through a continuum of expressiveness terminating at the most-extreme image for each construct. The position, shape, and movement of all elements were designed in-house, in accordance with established principles commonly used in the design of human facial expressions and their changes.

Images representing the most extreme intensity of each transforming icon were generated, as well as those representing 20% of the maximum intensity. These images were thereafter referred to as 1.0 and 0.2 intensity images, given the common scaled values ranging from 0.0 (neutral) to 1.0 (most extreme) underlying each transforming icon's continuum of expressiveness. Thus, two images for each of the six constructs were investigated.

In each trial offered to subjects for examination, there were two images, one of which corresponded to the construct (target) being investigated in that trial, and one of which corresponded to another (foil) construct. In no circumstances were the two images for a given construct set against one another for comparison and forced-choice by subjects. And no image ever went up against itself.

The order in which subjects encountered each construct was randomized. The position (Position 1 versus Position 2) that the image matching the construct appeared in was randomized. The foil image presented was randomly selected from all available foils. In some investigations, 1.0 intensity images might be set against 1.0 or 0.2 foil images, whereas in other investigation, only matching intensity level images (e.g. 1.0 vs. 1.0) were presented to subjects, depending on the nature of the investigation.

As outlined above, subjects could choose one or the other of the two presented images as their selection as to which image best answered the question, "Which face looks _____?" They had a third option, a separate button juxtaposed between the competing images, labeled "Neither" so as to allow subjects to opine that neither of the presented images looked to them to represent the target construct of a that trial.

Each subject was automatically presented with the next trial in a series in each study, such that each image being investigated was presented to the subject once for consideration as the "correct" answer. Thus, for example, in a study investigating 6 constructs with two images each under consideration, each subject would encounter 12 trials. In some cases, two or more sets of shape-shifting icons were investigated concurrently within one study; for example, a 6-transforming icon set might be investigated along with a 4-transforming icon set, for a total of 10 shape-shifting icons corresponding to 10 constructs investigated via a total of 20 images. In such a scenario, a target image would eventually face 18 alternative foils.

The datasets that follow describe the investigation and eventual passage of Level One face validity criteria by each of two intensity level images (1.0 and 0.2) for each of six constructs (Sadness, Anger, Happiness, Disgust, Surprise, and Fear) are presented below.

Core Transforming Icon Technology Face Validity Study via Validation Engine: Run #1

These data reflect our first effort to investigate the Core Transforming icon collection of six shape-shifting icons (anger, sadness, fear, disgust, surprise, joy). These six were investigated along with 7 additional shape-shifting icons reflecting other constructs, for a total of 13 constructs investigated with 2 images per construct (see above). Therefore, each image was set against 24 other images (2 each for 12 other constructs) which served as foils.

The high-intensity images needed to be correctly identified at least 90% of the time (i.e. in at least 90% of all trials) to be considered as Pass for further use and investigation. The low-intensity images needed to be correctly identified at least 50% of the time (i.e. in at least 50% of all trials) to be considered as Pass.

Run #1 (referred to as the Mixed Core & Insights Validation Study #1) resulted as follows:

| | |
|---|---|
| Afraid | 0.2: failed at 48.1% correct identification |
| | 1.0: passed at 92.0% correct identification |
| Angry | 0.2: failed at 17.7% correct identification |
| | 1.0: passed at 97.1% correct identification |
| Disgusted | 0.2: passed at 54.9% correct identification |
| | 1.0: failed at 87.5% correct identification |
| Happy | 0.2: passed at 85.3% correct identification |
| | 1.0: passed at 95.5% correct identification |
| Sad | 0.2: failed at 33% correct identification |
| | 1.0: passed at 92.8% correct identification |
| Surprised | 0.2: passed at 73.0% correct identification |
| | 1.0: passed at 91.7% correct identification |

Thus, we saw that two shape-shifting icons (Surprised, and Happy) passed both Level 1 criteria in this sample of 255 persons ages 16 through 65 residing in the US in a tested time period. In light of the large number of shape-shifting icons being studied in this initial validity investigation, those subjects were not required to rate all 26 images being investigated. Instead, they were given the option to discontinue at any time, beginning with Trial #1.

Incidentally, our findings were notable inasmuch as this sample produced an average of 14 trials each before discontinuance. Thirty-seven (37) percent of them completed all 26 trials, and 23% completed only 1 trial before discontinuance. This sample produced a total of 3544 observations (completed trials), for an average of 136 trials per image. This was considered an adequate general sampling for initial purposes, and it is a testament to the success achieved with our initial attempts to generate construct-representative images when we consider how many alternative foils each image had to compete with.

Core Transforming Icon technology Face Validity Study via Validation Engine: Run #2

These data reflect a second investigation of the same Core shape-shifting icons that we explored in Run #1, with a new sample of 151 US adults ages 16-65 years.

We eliminated the 7 shape-shifting icons from other collections and focused only on the 6 Core shape-shifting icons, as we were interested in learning whether failing shape-shifting icons in Run #1 were performing poorly only against low-intensity image foils, against high-intensity image foils, or both. We'd seen in Run #1, for example, that some low-intensity transforming icon images that failed performed well against high-intensity foil images, but less well against low-intensity foil images. We saw the reverse for some high-intensity images. For this run, then, subjects saw low-intensity images compete with only other low-intensity images (e.g., 0.2 Angry vs. 0.2 Happy), and high-intensity images were set against only other high-intensity image foils. Each image therefore was competing with only 5 other foils.

Although each image had to compete with a lower number of foils than in Run #1 (and thus might be expected to perform better simply by chance), we retained the same pass/fail criteria as in Run #1: the high-intensity images needed to be correctly identified at least 90% of the time (i.e. in at least 90% of all trials) to be considered as Pass for further use and investigation. The low-intensity images needed to be correctly identified at least 50% of the time (i.e. in at least 50% of all trials) to be considered as Pass. We believed this was defensible on the reasoning that the lower-intensity images faced stronger competition by being set against only other low-intensity images, whereas their performance against high-intensity images ought to be quite strong, if only because the high-intensity images had performed more strongly overall in Run #1.

Because there were only 6 shape-shifting icons (thus 12 images) being investigated, we required each subject to rate each image in this series, rather than giving them the option to discontinue early, as had been provided in Run #1.

Run #2 (referred to as the Intensity-Specific Validation Study #1) resulted as follows:

| | |
|---|---|
| Afraid | 0.2: passed at 51.7% correct identification |
| | 1.0: passed at 94.4% correct identification |
| Angry | 0.2: passed at 53.0% correct identification |
| | 1.0: passed at 95.6% correct identification |
| Disgusted | 0.2: passed at 78.8% correct identification |
| | 1.0: passed at 93.8% correct identification |
| Happy | 0.2: passed at 92.0% correct identification |
| | 1.0: passed at 95.6% correct identification |
| Sad | 0.2: failed at 48.3% correct identification |
| | 1.0: passed at 98.1% correct identification |
| Surprised | 0.2: passed at 88.1% correct identification |
| | 1.0: passed at 94.4% correct identification |

Thus, we saw that five of the six Core shape-shifting icons passed both Level 1 criteria in this sample of 151 persons ages 16 through 65 residing in the US in the tested time period. Sad's 1.0 image passed, but the 0.2 image feel just shy of the >=50% correct identification rate. This investigation suggested that the shape-shifting icons were performing well overall, and that success in Run #1 was not due only to the putative ease with which low-intensity images of any sort could be differentiated by viewers from high-intensity images.

Core Transforming Icon Technology Face Validity Study via Validation Engine: Run #3

In this iteration of the study, we ran a revised version of the Sad transforming icon alongside seven other shape-shifting icons we refer to as our Insights collection (reported elsewhere). The other five Core Shape-shifting icons had already each successfully reached our Level 1 criteria for face validity. In this sample of 251 U.S. persons ages 16-65 years, the Sad transforming icon was once again tested at high- and low-intensity image levels. It was compared against high- and low-intensity images representing seven other shape-shifting icons for a total of 504 trials.

| | |
|---|---|
| Sad | 0.2: passed at 52.8% correct identification |
| | 1.0: passed at 97.2% correct identification |

Core Transforming Icon Technology Face Validity Study via Validation Engine: Conclusion As a result of these multiple investigations, we established Level 1 face validity for the six Core shape-shifting icons, which represent the constructs of Sadness, Anger, Disgust, Surprise, Fear, and Happiness, for mixed middle-adolescence through adulthood in U.S samples.

Insights Transforming Icon Technology Set Validation: Design, Results, and Data

Having successfully validated the Core transforming icon set (per above), we endeavored to develop a second set of shape-shifting icons that might be useful for a variety of applied settings, including those that might ask business customers to describe their feelings about brands, about services they have received from them, about products purchased from them, and about their alternatives. We again employed the Forced-Choice Validation Engine paradigm to pursue Level 1 face validity for each of several shape-shifting icons designed for this purpose. They included Excited, Delighted, Meh, Disappointed, Frustrated, Worried, Surprised, and Disgusted. Note that two, Surprised and Disgusted, were derived from those of the same constructs as in the Core transforming icon set (above). Surprised and Disgust were adopted as a potential feelings one might reasonably register in response to behaviors by a business or its representatives, about characteristics of the business itself, or representative characteristics of the business (e.g. website theme, logo design). The other Core transforming icon constructs were deemed less relevant with respect to the language people might naturally use to describe their feelings about businesses. For example, we supposed that people were more likely to report feelings of disappointment (which has a basis in sadness) than they were to report sadness per se.

Therefore, we chose other emotion constructs to represent different types of feelings one might naturally register about businesses and their products and services. These included two positively-valenced constructs, Excitement and Delight, which would transition across time to the constructs Excited and Satisfied, in an effort to capture two levels of arousal within the positive valence domain, as Excited and Delighted proved in several trials to be too easily confused with one another.

We also chose to develop Worried (based in fear), Disappointed (based in sadness), Frustrated (based in anger), and Meh, a special case construct of our own theoretical offering, as it is not a construct in and of itself found in other models of emotion, but which seemed to capture at least one important emotion domain not captured by the others.

As a result of many trials, we defined a set of Insights shape-shifting icons that might be deployed in additional applied and theoretical studies for further development. Results illustrated the 1.0 and 0.2 intensity level images from shape-shifting icons developed to reflect each of the constructs (Excited, Delighted/Satisfied, Meh, Disappointed, Worried, Frustrated, Surprised, and Disgusted) through a succession of validation runs, along with the degree to which the research subjects (which were U.S. persons ages 16-65, typically 250-300 at a time) agreed that the image represented the construct when the image was set against images from the other constructs, consistent with the validation efforts employed with the Core transforming icon set.

For these trials, each transforming icon was identical in size, shape, color (with one exception, Frustration), number/configuration of elements designed to resemble human eye whites, pupils, eyebrows, and mouths, and the baseline Neutral image representing the lowest-intensity value (0.0 on a scale of 0.0 through 1.0) of each construct investigated. What was left then to vary was the shape, location, and sizes of the facial elements as they transformed from the Neutral expression through a continuum of expressiveness terminating at the most-extreme image for each construct. The position, shape, and movement of all elements were designed in-house, in accordance with established principles commonly used in the design of human facial expressions and their changes.

Images representing the most extreme intensity of each transforming icon were generated, as well as those representing 20% of the maximum intensity. These images were thereafter referred to as 1.0 and 0.2 intensity images, given the common scaled values ranging from 0.0 (neutral) to 1.0 (most extreme) underlying each transforming icon's continuum of expressiveness. Thus, two images for each of the eight constructs were investigated.

The method for investigation was otherwise identical to that employed with the Core transforming icon set validation (see above). A total of 10 trials were conducted, and a set of eight Insights shape-shifting icons were decided upon for deployment. Some 1.0 images did not achieve the desired 90%+agreement levels; in some cases, additional development work for refinement is planned. Meh is an exception in this regard.

The Meh transforming icon was designed to capture a relative lack of feelings between those traditionally described as positive in valence (e.g. delight, excitement, satisfied) and those traditionally described as negative in valence (e.g. anger, disgust, fear, frustration, etc.). As such, the Meh transforming icon was intended to capture indifference—literally, a lack of care, concern, passion or other feelings about a target aside possibly from boredom. However, we also acknowledged that people in everyday usage, Meh can express a type of passive acceptance, an acquiescence, to certain things that does not literally represent indifference. Instead, it can also represent a very low level of arousal, concern, or investment in a phenomenon that might be very slightly tinged in a prevailingly positive or negative way. The effort was to create an expression that captured the statement, "meh, I really don't much care" with the "much" qualifier being important. It was not known whether or not people would hope to express a degree of intensity of this subjective experience. The efforts to create an expression with a high degree of agreement that it represents Meh were frustrating, inasmuch as we did not in the 10 trials reported here, create a face with higher than 80% agreement. Notably, however, the expressions we created were generally rated as highly at 0.2 as they were at 1.0 intensities, suggesting that the expressions should not be intensely expressive lest they begin to clearly suggest some feeling other than Meh. At present, the Meh transforming icon is simply a low-intensity expression that has reasonable agreement levels at a "high" intensity in both the designed form and its mirror image; these are set as polarities such that in its current form, it has no true zero, and intensity is set as 0.5 for all points along the continuum of expressiveness between the poles of movement. Thus, it is distinct from the other shape-shifting icons, while we can develop a new one to be more representative of the construct and which might also allow in some instances for intensity registration.

Expansion Sets: CX/CR Insights transforming icon technology Set Validation Design, Results, and Data Having successfully validated the initial Insights transforming icon set, we then sought to expand the variety of shape-shifting icons that might be used in various Customer Experience (CX) and Consumer Research (CR) applications.

As with previous Insights shape-shifting icons development, we employed our Forced-Choice Validation Engine paradigm to pursue Level 1 face validity for an expanded set. The expanded set conforms to the general graphical details (round object with facial features, colors consistent with previously-validated shape-shifting icons, etc.). Extensive examples of the validation process were presented regarding the development and validation of Core shape-shifting icons.

Our first expansion set was developed primarily to serve the needs of those seeking to know people's emotional reactions to advertising content, including elements (e.g. images, statements, sound bites) and/or ads in their entirety. The shape-shifting icons designed for this purpose might in some instances serve in response to the question, "How does this make you feel?" This question is meaningfully distinct from a related question, "How do you feel about this?" as this question could reflect a feeling-level summary judgment about the ad or its element(s), as opposed to a feeling provoked by the ad. By way of illustration, one might decide after seeing/hearing it that they Like it. "Like" is a feeling about the ad, as opposed to a feeling one experiences during the ad. Though there can certainly be overlap in the feeling states one might experience during the ad, or prompted by one or more of its elements, the summary feeling of Liking of the ad might occur despite the ad's having prompted Sadness or Disgust. One might Like an ad aimed to present the dangers of tobacco use that is deemed relevant, informative, and persuasive, even if the ad content in whole or in part prompted feelings of Disgust. This expansion set included Happy, Sad, Bored, Excited, Disgusted, Worried, Curious/Interested, Annoyed, and Confused, though other emotions might also or alternatively be considered for this purpose.

Faces which have passed at the previously-established Level 1 criterion levels via such Validation process include Annoyed, Bored, Confused, Disgusted, Excited, and Worried. Others have passed in previous studies, and are already considered validated on their own merits, though at one or another intensity levels have not passed as strongly in this series of studies; these include Sadness and Happiness. One, Curious, has proven difficult to validate and has not yet passed Level 1 criteria in any study, and so is not yet available as part of this expanded set. It should be understood from the complete disclosure herewith that additional transforming icons may be created and validated within the broader concepts of the presently disclosed subject matter, all of which are intended to come within the spirit and scope of the disclosure.

Two shape-shifting icons in this expanded set bear specific mention otherwise: Bored, and Confused. Bored in this set is special inasmuch as, in its current iteration, it does not measure a spectrum of intensity the way all others thus far validated do. This is because our investigations thus far suggest that Boredom perhaps is not felt with varying levels of intensity the way other emotions are. That is to say, it appears that this construct may be one that is felt more dichotomously, as either present or absent, without meaningful distinctions along a continuum. Previous efforts to validate a Boredom transforming icon have, interestingly, demonstrated that various more intense expressions do not reach the same levels of agreement as less intense expressions do. Our conclusion thus far is that one might feel boredom in the absence of arousal, whether that arousal is positive in valence or negative in valence, in response to stimuli. While the felt sense of boredom might grow in unpleasantness the longer it persists, the brief sensation of boredom as a reaction to ad content might not be particularly intense.

Confused is also special, inasmuch as it incorporates transforming elements in the form of "swirly" lines surrounding the top of the face that are similar to those frequently employed by animators to convey dizziness, as can be seen in the link above. These are not present at all at the baseline neutral expression of Confused, but appear and begin to grow in apparent prominence as the transforming icon is adjusted to convey a more intense expression. This addition proved to be significantly helpful in capturing this construct and particularly in distinguishing it from the other constructs in this expanded set.

Predictive Validity: the Relationship of Customer Emotion, NPS Ratings and Behavior Given successful validation of an initial Insights transforming icon collection, one can establish evidence that shape-shifting icons have utility in the measurement of customer engagement. Specifically, it is anticipated that some subset of the Insights shape-shifting icons collection can be used to explain the ratings provided by persons responding to the Net Promoter Score question, "How likely is it that you would recommend our company/product/service to a friend or colleague?" Similarly, emotion measures can serve as the foundation for recommendations to brand managers and other business administrators for improving their brand's performance.

Guiding Theory Underlying NPS & Emotion Relationships: Behavioral Economics

Underlying any efforts that compare and/or combine the NPS model with our transforming icon Insights Model is an assumption that there is at least a significant and meaningful correlational relationship between NPS ratings and emotion reports at the individual reporting level, and furthermore that there is a causal relationship between the two. A putative causal relationship is the basis for actionable insights in helping people get closer to actionable insights with a brief, efficient, engaging measure that taps motivations and predicts behaviors. This reflects a larger theory of the role of emotion in motivation and behavior—namely, that classes of emotions are predictably tied to differing types of motivations and generalities of behavior. As such, there are various assumptions that are in need of empirical investigation. These can be stated as a series of hypothesis.

Hypothesis 1: We assert that people's NPS ratings (i.e. their endorsement of 0-10 in response to the NPS question) is meaningfully related to their feelings about the company/product service targeted by the NPS question, at any given point in time. That is to say, we believe one variable can help to predict another. This is a correlational proposition.

Hypothesis 2: We also assert that people's NPS ratings about the company targeted by the NPS question are determined, at least in significant part, by their feelings about the company. This is a causal proposition.

Hypothesis 3: We also assert that we know, or can determine, which emotions are most salient to assess to support Propositions 1 and 2. This is a domain expertise proposition.

Hypothesis 4: We also assert that the salient emotions can be captured and measured validly and accurately by the transforming icon technology Platform. This is a psychometric measurement proposition.

Hypothesis 5: We also assert that there is a systematic—possibly ordinal—relationship among the salient emotions, such that the distributions of intensities (represented in whole or in part, e.g. by measures of central tendency) of those emotions reported by persons about the brands in question could be plotted and found to correspond meaningfully along a one-dimensional line formed by the ordinal (possibly interval/ratio) rankings reported by those same persons in response to the NPS question (see above). This is a systematic relationship among emotions proposition.

Such presumed relationship among emotions may have some a priori support by researchers who have asserted a theoretical grid formed by two axis, where one horizontal axis (valence) has positive and negative extensions past a neutral position that is neither positive nor negative (neither of which having a set maximum value), and one vertical axis (arousal) represents a dimension intersecting the first at a 90 degree angle such that above the intersection the vertical axis represents higher and below the intersection represents lower, those being relative to one another but with no set maximum value. If correct, this two-dimensional layout could allow various emotions to be plotted with respect to arousal and valence, and then selected with respect to a theoretical distance (represented as a vector) from the intersecting point of the two axes and aligned in an ordinal array according to those supposed distances.

Hypothesis 6: We also assert that certain emotions, being positive in valence and corresponding to what have been described (by Ira Rosen, PhD) as "contacting" emotions, underlie motivations and behaviors by customers that would be considered to greater and/or lesser degrees as beneficial to the brand posing the NPS question. Furthermore, we assert that certain emotions, being negative in valence and corresponding to what have been described as "distancing", "rejecting", and "attacking" emotions, underlie motivations and behaviors by customers that would be considered to greater and/or lesser degrees as detrimental to the brand posing the NPS question. This is a beneficence proposition.

Hypothesis 7: We further assert that people's feelings about other key dimensions, e.g. their most recent experience with the company targeted by the NPS question, help meaningfully to determine the NPS rating they provide at a given point in time, and that these feelings can be captured and measured by the transforming icon technology Platform. This is the contextual proposition. NOTE: This proposition subsumes the same additional propositions 1 through 3 for each additional question we add to the model, and could be investigated similarly.

There then follows a series of downstream propositions that are presumably of most interest to businesses, and these are key to the larger success of the transforming icon Insights Model as a demonstration of the value of emotion data/insights.

Derivative Hypothesis 1: We assert, by inference, that successful efforts by the business to move individual customers from distancing, rejecting, and damaging classes of feelings about the business to the contacting feelings class about might result in higher NPS ratings from those persons in the future. This is the intra-individual change proposition.

Derivative Hypothesis 2: We assert, by inference, that businesses can identify and successfully implement changes that result in a greater proportion of contacting feelings in a cross-section of their customers at any given point in time, and that these might result in higher NPS ratings from those same people. This is the systemic change proposition.

Preliminary Evidence from Research with NPS and Transforming Icon Technology Ratings We have conducted a number of studies pitting transforming icon technology against the commonly-recognized Net Promoter Score (NPS) system to compare and contrast people's responses to the NPS question "How likely are you to recommended (Brand) to a friend or colleague" and their endorsement of feelings about brands.

In one illustrative study, we asked 399 U.S. adults ages 18-35 (via Amazon Mechanical Turk, an online medium for reaching registered respondents who have consented to participating in polls, surveys, and questionnaires) to provide their NPS rating and their (presumably most salient) feeling about a variety of brands, namely: Apple, United, Uber, Wells-Fargo, and Comcast.

To answer the question, "How do you feel about (Brand)?" the respondents were provided the transforming icon technology Insights collection of shape-shifting icons, excluding the Worried transforming icon, as it was deemed an unlikely response, and including two previously-validated shape-shifting icons that had not been deployed in other contexts: Love, and Hate. Hate was substituted into the set in place of Disgusted, as an emotion that we imagined might resonate with people more so than Disgust. Thus, the expanded transforming icon technology response set included Love, Delighted, Satisfied, Meh (indifference), Disappointed, Frustrated, and Hate.

As this was a within-subjects design, each respondent was first asked to identify each and every brand (of the five presented) with which they were familiar. Then, in randomized order, they were then asked five compulsory questions about each brand they endorsed. The first asked them to show, with one of the variety of shape-shifting icons (above) how they feel about the brand. If they did not organically register the intensity of the feeling type they specified, they saw a prompt to do so. They were then asked the NPS question as to how likely they were to recommend that brand. Third, they were asked how many times they had said or written something negative about that brand within the most recent 12 months. Fourth, they were asked how many times they had actually recommended the brand. Finally, they were asked to report their background mood with a variety of four Mood shape-shifting icons (previously validated), namely: Good, Down, Grumpy, and Tense.

The resulting data set included 1767 brand-focused NPS ratings and an equal number of responses to the other questions. For analysis, emotion type, emotion intensity, NPS numeric ratings (0 to 10), behavioral tallies and mood type and intensity ratings were all recorded. The third and fourth questions were combined into a Behavioral Index, reflecting the net total of negative behaviors subtracted from the positive behaviors. The Behavioral Index scores ranged between −6 and 6.

Figure 10:
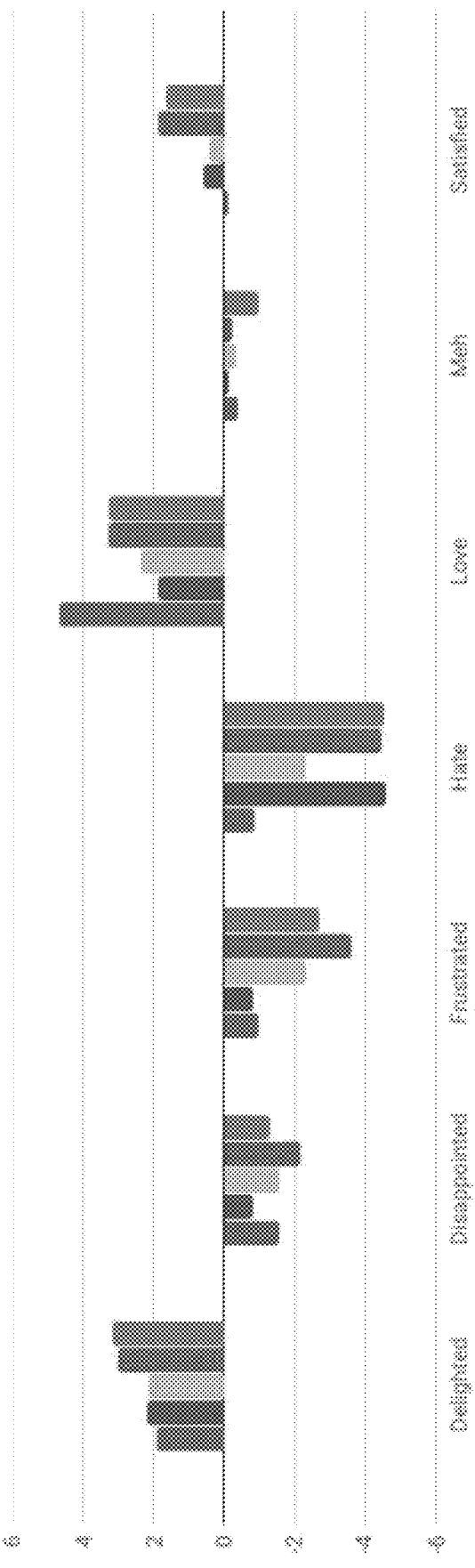
FIG. 10A is a bar graph illustrating how various reported feelings among study participants corresponded to differing levels in a Behavioral Index net count, with different bar sets for each emotion group representing each of five intensity ranges registered.
FIG. 10B is a chart reflecting the breakouts of the five non-neutral/non-resting intensity groups represented in the FIG. 10A bar graph data.

As referenced below vis-à-vis FIG. 10A, the various feelings corresponded to differing levels in the Behavioral Index net count. For example, Hate was associated with the lowest net number, reflecting many more reported negative behaviors associated with the brands (aggregated) than positive behaviors. Love was associated with the highest Behavioral Index net counts. Meh produced only very slightly positive overall Behavioral Index counts. Other emotions fell in-between, in an ordinal ranking that accords with other studies which are not reported here. The colored bars of FIG. 10A represent within each emotion, the Behavioral Index score associated with each of five intensity ranges registered for each emotion by the overall group. The intensity value of 0.20 is not represented, owing to the fact that the 0.20 intensity value was the "resting" state at which each transforming icon, when selected, was portrayed, and subjects were compelled to move the intensity adjustment mechanism (in this study, a movable scroll or slide) away from the resting point to some degree. FIG. 10B is a chart reflecting otherwise the breakouts of the five non-neutral/non-resting intensity groups.

Associations between emotions and behaviors were demonstrated to be statistically significant in most all cases. FIG. 11 illustrates a chart representing the correlation (r) with number of behaviors for positive and negative valences for each of seven emotions tested vis-à-vis the subject matter represented by FIGS. 10A and 10B. Each of the highlighted cells was significant at the $p<0.05$ level.

Figure 12:
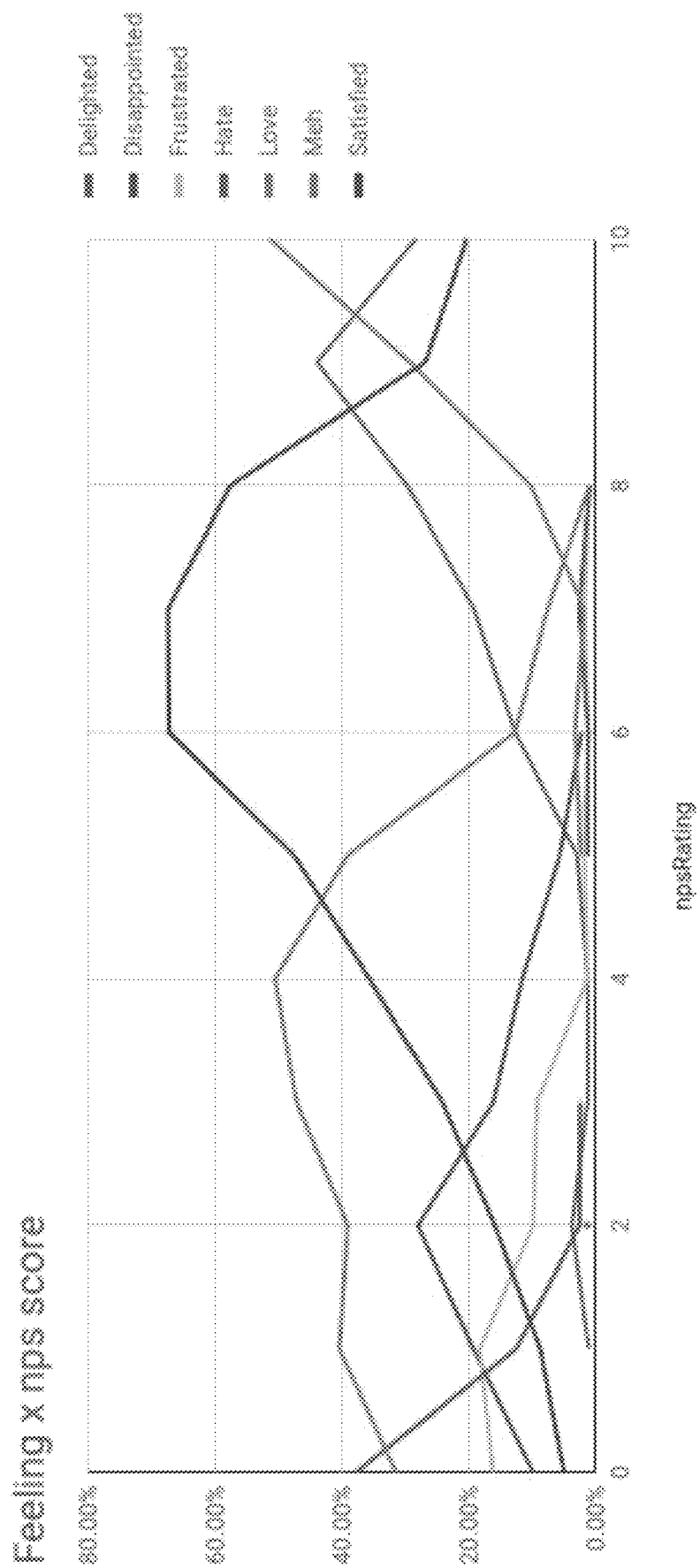
FIG. 12 is a graph of aggregated sample data relative to the subject matter of subject FIGS. 10A, 10B, and 11, demonstrating the percentage of respondents reporting each emotion at each point along the Net Promoter Score (NPS) rating scale of 0 to 10.

In the aggregated sample, the graphic of FIG. 12 demonstrates the percentage of respondents reporting each emotion at each point along the NPS rating scale of 0 to 10. As can be seen, people reporting NPS rating 10 (the highest endorsement of likelihood to recommend) reported a mixture of Love, Delight, and Satisfaction. The same was true at NPS rating 9, and almost entirely true at NPS rating of 8. Notably, however, the NPS rating System could alternatively characterize only the 9's and 10's respondents as "Promoters" and 8's (as well as 7's) as "Neutrals." Satisfaction was reported mainly between NPS ratings of 5 and 8, but was not absent among those who reported NPS ratings of 0 through 4. Notably, the NPS system characterizes anyone reporting an NPS rating of 0 through 6 as a Detractor. Hate was reported only by those reporting an NPS rating of 0 through 3, mainly at 0. While Love was reported by subjects mainly at NPS ratings 9 and 10, it was also reported by those at NPS rating 8, 7, 6, and 5. mainly among those at 9's and 10's. But Delight, an apparently less-affiliative feeling than Love, was reported by those registering NPS ratings of 4 through 10. Satisfaction was reported by respondents at each and every one of the NPS rating levels 0 through 10.

Figures 13A, 13B:
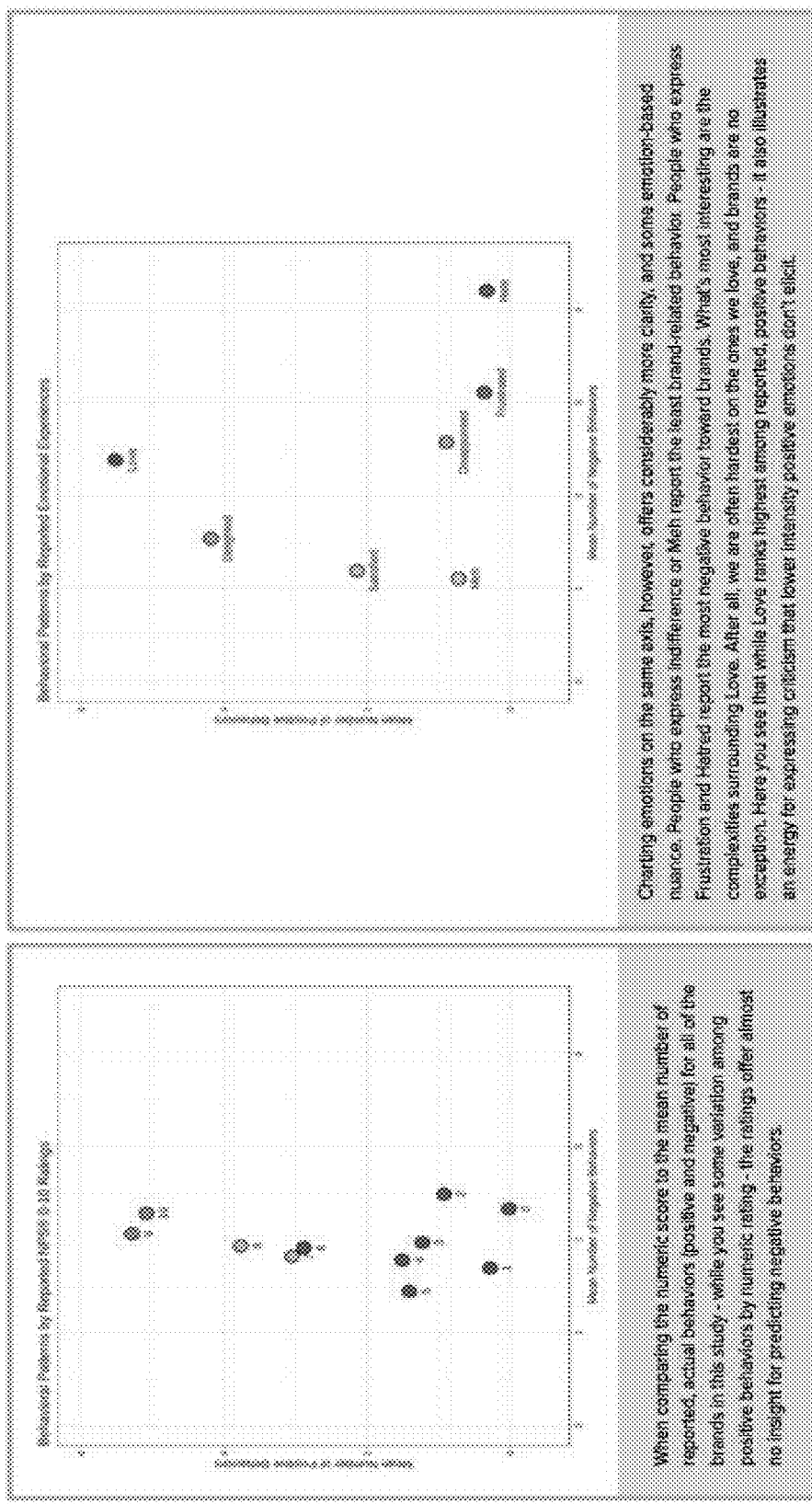
FIGS. 13A and 13B illustrate respective plots of data from FIGS. 10A through 12, showing that while the NPS ratings demonstrate an essentially linear relationship between NPS ratings 6 through 10 with respect to mean numbers of positive behaviors, ratings of 0 through 5 do not.

Another visualization of such findings is even more clear, per subject FIGS. 13A and 13B. Such plots show that while the NPS ratings demonstrate an essentially linear relationship between NPS ratings 6 through 10 with respect to mean numbers of positive behaviors, ratings of 0 through 5 do not. Furthermore, the mean number of overall negative behaviors among those registering NPS ratings of 6 through 10 were essentially the same as the average among NPS ratings of 0 through 5. In contrast, the types of positively-valenced emotions respondents reported about the brands demonstrated a clearer, curvilinear relationship to positive behaviors and a wider, more linear relationship between negative emotions and negative behaviors, without meaningful change in mean positive behaviors. People who expressed Meh (indifference) toward the brands reported the fewest number of positive and negative behaviors, in line with expectations, suggesting the lowest overall engagement with the brands.

Figure 14:
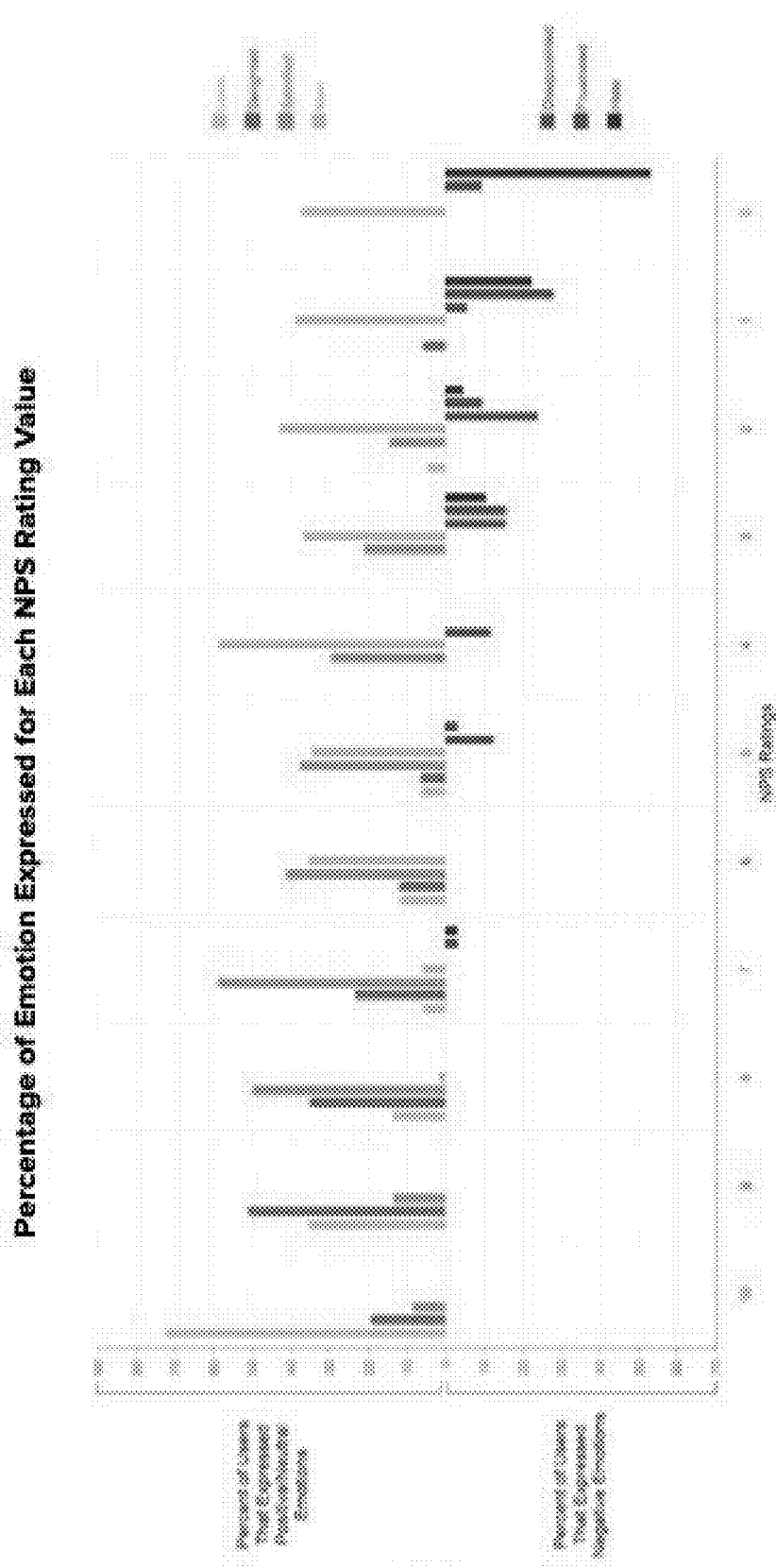
FIG. 14 illustrates bar graph data reflecting that respondent's reported NPS score demonstrated non-linear associations with the emotions endorsed about the brands.

This trend can be seen within individual brands, as well, as with Apple, below. In FIG. 14 bar graph data, we see that people's reported NPS score demonstrated non-linear associations with the emotions endorsed about the brands. Meaningfully, such profiles differed from one brand to the next.

Evolving the Transforming Icon Technology GUI: Color, Color Gradient, and Non-Linear Features Movement Development involved experimenting with alterations of some of the transforming icon technology UI graphic characteristics (e.g. the primary color scheme), and added additional features to the Scale Builder to create more nuanced movements of the elements within a graphic, along with new capacities, including alterations to border stroke color/width, modifiable opacity and transforming thereof to an entire image or to elements therein, etc.

Such development also involved designing and testing several new shape-shifting icons loosely defined as "clinical," reflecting their intended use specifically among healthcare researchers and providers to capture, communicate, and measure constructs frequently reported by healthcare patients and in epidemiological studies. These constructs include, but are not limited to, anxiety, depression, confusion, nausea, irritability, and more.

We also designed and used another embodiment of an initial face validity investigation, intended to allow more rapid test acceptability of a given design proposal as a representation of a target construct, for particularly involving development of shape-shifting icons to represent constructs that have minimal, if any, history of being empirically validated as having consistent facial expression representation.

Rather than asking study respondents to choose in a forced-choice paradigm which—if either—of two images best represent a given construct, and testing a proposed construct against four or more alternatives (see above), we alternatively devised and used a simpler method to allow people to register qualitatively whether, and to what extent, a given design proposal appeared to represent a construct. Such second validation embodiment is referenced herewith as the Preliminary Validation Engine. A self-explanatory example of the Preliminary Validation Engine user interface subjects is displayed in FIG. 15A.

In some trials, validation study respondents were shown one target construct image at a time, and were asked to what degree the image looked like the target construct, given four response options: Definitely, Mostly, Somewhat, and Not at all. They were allowed only one response per target construct image. However, they could indicate which, if any, emoji they might use to express the target construct. The open entry field allowed them to describe emojis qualitatively, by name, or by cutting and pasting-in an example emoji image.

In such second embodiment of a validation paradigm, we set pass/fail criteria as follows: an image was determined to meet minimal face validity acceptability if and only if 80% or more of all respondents chose "Definitely" or "Mostly" to describe the degree to which they saw the target construct image as a representation of the target construct. A target construct design was determined to represent a "strong pass" if both of two conditions were met: 1) 80% or more of all respondents chose "Definitely" or "Mostly" and 2) 50% or more of the respondents chose "Definitely". Therefore, a design would not be considered a pass if 50% or more chose "Definitely" but the combined "Definitely" and "Mostly" categories did not total 80% or more of all responses.

This paradigm embodiment allows the user to display several design studies as alternative options to represent a given construct. Those design options might differ in terms of intensity levels from a transforming icon continuum, as is the case in our forced-choice paradigm. They might differ instead by feature changes, such as our traditional green background color versus a new, more yellow option.

Clinical transforming icon technology Library

We ran preliminary validation per below for the following shape-shifting icons using the original green face color:
anxious
confused
depressed
dizzy
energized
fatigued
irritated
nauseated
in pain/pained Four of the clinical shape-shifting icons designs (anxious, dizzy, irritated, and nauseated) passed preliminary validation. Confused, depressed, energized, fatigued, and pain did not pass preliminary validation.

In light of feedback received during some preliminary validation runs that the green color did not work well for the constructs, we tested a hypothesis that some of the construct target faces might be more recognizable if they more closely resembled traditional emoji coloration.

We tested 32 commonly-available emojis through the Preliminary Validation Engine and found that 7/9 clinical constructs (anxious, depressed, dizzy, energized, irritated, nauseated, in pain) passed validation at the accepted criterion level.

Figure 15B:
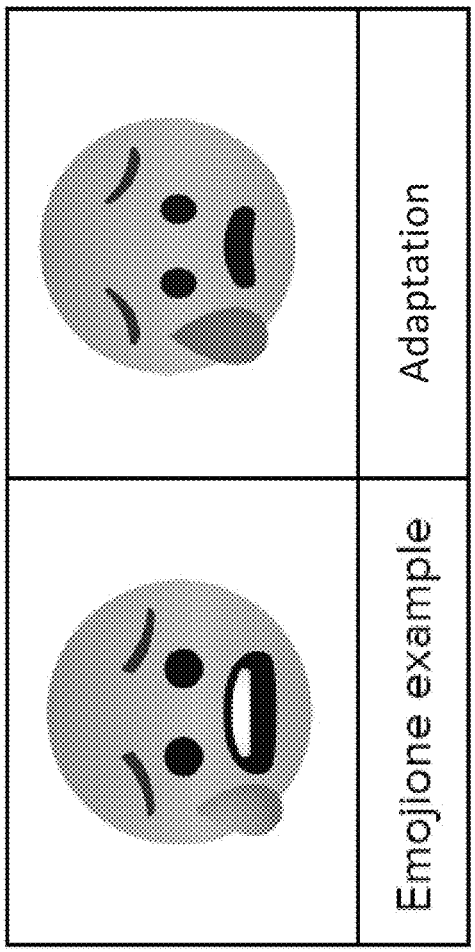
FIG. 15B illustrates in chart form representations of a comparison between an initial example versus an adaptation version of the "same" icon, for testing and validation purposes.

We then used 3 of those emojis (i.e. those tested to represent anxiety, depression, and pain) as models for a new design language for use as clinical shape-shifting icons. These were modified to be distinct from those tested, while still somewhat resembling the emojis which passed validation. FIG. 15B in chart form represents comparisons between initial examples versus adaptation versions of the "same" icon. We ran new validation trials using the transforming icon adaptation and each of the three new designs passed validation.

SUMMARY & CONCLUSIONS

The transforming icon technology is comprised of a novel graphical interface, scaled quantification and a robust data analytics system. It is designed first and foremost as a means for people to accurately communicate subjective experiences that are otherwise difficult to capture and convey, such as emotions, mood states, and physical sensations such as pain and nausea.

The presently disclosed subject matter provides an engaging graphical interface to provide clear, concise, and efficient data capture based on our natural capacity to "see" the type and intensity of their experiences in the interface, which can be adjusted until that moment of resonance is found. The quantification occurs in the background.

Likert scaling and 5-star systems, commonly used in survey and feedback systems, rely on potentially ambiguous terms and require people to quantify their own experiences in order to share them. Emojis are imprecise and often confusing non-verbal graphical representations. And both text scraping and biophysical data (e.g., facial decoding systems) rely entirely on inferential methods in an attempt to discern people's subjective states. Transforming icon technology as described herein avoids each of such limitations.

Figure 15C:
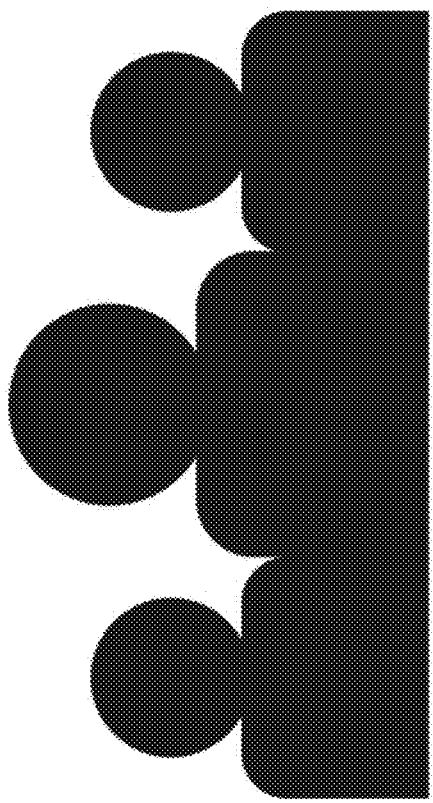
FIG. 15C illustrates an exemplary embodiment of a GIF for a Loneliness transforming icon, which helps to illustrate the potential use of transforming icon technology beyond facial expressions.

The presently disclosed subject matter also describes how to support the development, validation, refinement, and evolution of the disclosed shape-shifting icon technology. Evidence for construct validity and behavioral prediction utility are described, along with a core library of shape-shifting icons representing basic mood and emotion constructs commonly recognized by key theorists, which have been validated. In addition, further presently disclosed shape-shifting icon libraries and extensions appropriate to customer relations and consumer research implementation are discussed. Further transforming icon libraries in accordance with presently disclosed subject matter can address communicating and measuring clinical constructs in healthcare environments, and additional transforming iconography is intended to come with the scope of the present disclosure. For example, FIG. 15C illustrates a GIF of a Loneliness transforming icon, which helps to illustrate the potential use of transforming icon technology beyond facial expressions, where changing degrees of separation between the illustrated components can represent the respondent's degree of Loneliness.

Hypothetical Case Study Example

The following uses fictitious information and hypothetical responses for an example. In other words, all example information and/or example-supporting data throughout this specification is entirely fictitious and only for purposes illustration and example, and not intended as any limitation on the broader concepts presently disclosed.

In particular, this hypothetical case study example includes a technical explanation of how to calculate what is referenced herein as a roll-up or composite score of affective factors or determinants.

The disclosure is intended as just one possible example of calculation, encompassed by the broader disclosure herewith. For example, additional methods encompassed herewith may for some embodiments may involve more "matured" database sets which draw from additional individual scores data and apply machine learning to better understand the relationships and influence of various selected and/or tested factors.

In this hypothetical case study example, Patient X is scheduled for outpatient hip replacement surgery in 2 weeks. As part of the pre-surgery planning, the orthopedic team has Patient X complete an assessment, using presently disclosed technologies to measure their risk level for various selected specific affective determinants (factors) concerning the overall health of Patient X. Assume for this example that the risk scores based on tested feedback from Patient X for each such selected factor are shown in Table 3 herewith:

TABLE 3

| Selected Example Affective Factor/Determinant | Score based on Assessment Feedback |
|---|---|
| Sick-Well | 47 |
| Pain | 87 |
| Stress | 53 |
| Anxiety | 76 |
| Loneliness | 21 |
| Irritability | 59 |
| Depression | 64 |

Per the exemplary embodiment disclosed herewith, the "roll-up" scoring of all the seven selected Affective Factor/Determinant Assessments (as shown in Table 3 herewith) amounts to 58 in this instance for Patient X. One example of obtaining such scoring is as follows.

In this example, seven Affective Factor/Determinant Assessments were selected for use. In various embodiments, there may be more or fewer numbers, or a different grouping of seven selected factors/determinants. In this example, all seven were assigned equal weights, and a simple calculation was used to derive a mean value of 58.142857, which for illustrative purposes has been rounded to the integer 58. In other embodiments, various weighting factors can be applied to various of the factors/determinants, and/or other approaches to calculations can be practiced with the underlying assessed values (whether weighted or not). The "scoring" value could be assessed and reported in some different fashion, such as falling into quintets or thirds with respect to risk, and reported within such groupings with color or textual cues (for example, high, medium, low risk if thirds used).

Furthermore, scoring may be normalized to any desired scaling, such as a consistent range of 0-100 (though different ranges could be used in various embodiments). In some alternative systems, the indexed range may comprise a scaled and normalized range from between 0 and a predetermined top scale number. In some such instances, the predetermined top scale number falls into a range from 1 to 100.

Presentation of results could be characterized in various ways, including labeling which makes use of proprietary branding, none of which forms any particular part of the presently disclosed subject matter and/or technology. In general, the concept is that in some labeled fashion the scoring can be reported via an end-user display or some form of report that expresses scoring or ratings with reference to obstacles regarding health achievement or likelihoods on a scale of same. In some instances, the individual results can be assessed against anonymized results from numerous individuals (with common/similar backgrounds or otherwise) to weight relative to standard population responses and risks. In other words, in some instances use may be made of database tables of prior results which assessed the same factors currently being assessed for Patient X.

In other words, in different embodiments of the presently disclosed subject matter, particular methodology in respective instances may incorporate variable values, variable maths, variable purposes, and variable means for subsequent representation/reporting/display, and the presently disclosed subject matter is not intended as being limited to the specific example shown and discussed herein.

An underlying aspect is that the factors/determinants as assessed in each instance using graphic displays which may in some instances be referred to as transforming icons or shape-shifting icons. There is no intended limitation on the shape or appearance of the graphic icons used. However, they are all intended as continuously variable or movable by a patient being assessed, in order to express their responsive feelings to the factor in question. Furthermore, the range of such variable expressions has been "validated" in the context of the presently disclosed subject matter, so that meaningful underlying or raw results may be obtained, which are then variously composited as presently disclosed, to provide composite scoring in the subject context.

Thought of in another way, such transforming or shape-shifting icons may be described as user-adjustable dynamically-manipulatable digital graphic displays rendering scaled values to capture and measure subjective experiences. One example of such technology is provided by U.S. Pat. No. 9,959,011, the complete disclosure of which is incorporated herein by reference and for all purposes. In general, such subject matter also relates to means by which these dynamically-adjustable images are created, which involves two or more differing vector graphic images are entered into our interpolation engine, which then yields one image that is continuously variable for all representative points between any two of the images entered. The scaled representation and quantification can be linear, logarithmic, or of other mathematical functions.

Notably, the dynamically-adjustable images can be configured to be relatively language-agnostic, culture-fair, and highly engaging.

Considered yet another way, it is not intended that there is only one way to calculate an exemplary roll-up score per the presently disclosed subject matter. In a broader sense, the presently disclosed subject matter makes use of the herein-described transforming or shape-shifting icon technology in order to collect data (assess) for a patient's responsive feelings for a selected grouping of affective factors or determinants. The subject technology allows such feeling or emotional-based responses to be quantified in a precise fashion. Various embodiments of grouped underlying factors may be used in particular implementations of the present subject matter, and then selected mathematical approaches may be practiced, to generate a meaningful roll-up scoring of those affective factor assessments. Such derived scoring values may in some instances be presented in conjunction with various adjunct data, such as used in additional/subsequent calculations in conjunction with other values, such as those created to represent demographic, social factor assessments, biometric, survey, geographical, time, device type, operating system, and/or other variables, to create data gathering models useful for a variety of purposes both currently known/projected and for future purposes. For example, a form of assessment may be made for various social factors/determinants and a similar roll-up score created for a composite of such data, which is then integrated with the affective factors roll-up score to arrive at an overall scoring that addresses the broader likelihood or opportunity for particular patient to achieve determined goals.

The presently disclosed subject matter might be of potential interest to various users, including potentially insurance carriers to improve the average services cost per patient through better adherence and outcomes, which might in some instances enable the practice/organization to increase profit/patient and/or receive a greater reward percentage for high performance. Another segment which might have interest could be healthcare systems and small healthcare groups, for more effectively providing their time-starved health providers with actionable insight. Also, the pharmaceutical industry might have an interest in that some reports indicate perhaps as much as $300 Billion in unfilled Prescriptions.

While the present subject matter has been described in detail with respect to specific embodiments thereof, it will be appreciated that those skilled in the art, upon attaining an understanding of the foregoing, may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A methodology for predictively determining a patient's likelihood to adhere to a healthcare treatment plan for such patient, comprising:
creating a survey comprising a plurality of survey items related to selected determined obstacles to adherence;
interactively conducting the survey for a given patient by having the patient use a movable feature of a graphical interface on a display to respectively capture and definitively measure through non-verbal communication the patient's subjective experiences for each of the plurality of survey items, to form a set of data for the given patient for the corresponding plurality of survey items, wherein the graphical interface comprises digital graphic shape-shifting icons for such patient to view on said display, with the patient using the movable feature to manipulate the appearance of each respective icon through a range of appearances thereof so that it reflects the self-reported intensity of how such patient subjectively feels in response to each item of the patient survey; and
assessing the patient's set of data to determine a relative score for such patient for likelihood to adhere to a healthcare treatment plan.

2. A methodology as in claim 1, wherein the definitive measurement captured with each icon corresponds directly to the final point of manipulation established by the patient through such range of appearances in response to a particular survey item.

3. A methodology as in claim 2, wherein the shape-shifting icons are pre-validated for a selected population of patients in which the given patient is a member, to validate that each icon and its range of appearances represents the subject matter of its associated item and attendant range of intensities thereof.

4. A methodology as in claim 1, wherein the graphical interface renders scaled values to capture and definitively measure subjective experiences by having the patient use a movable bar to manipulate at least one of each respective icon.

5. A methodology as in claim 1, wherein assessing the patient's set of data includes establishing a predictive score for the given patient indexed relative to ranges of scoring of sets of data for responses to items involving the same shape-shifting icons as have been used in the survey for the given patient and pre-validated for a selected population of patients in which the given patient is a member.

6. A methodology as in claim 1, wherein assessing the patient's set of data includes establishing one of a relatively high, medium, or low probability of adherence to a healthcare treatment plan for the given patient.

7. A methodology as in claim 1, wherein assessing the patient's set of data includes establishing a specific score within an indexed range to relatively assess the probability of adherence to a healthcare treatment plan for the given patient.

8. A methodology as in claim 7, wherein the indexed range comprises a scaled range from between 0 and 100.

9. A methodology as in claim 1, further including reporting the determined relative score to at least one of the given patient, healthcare staff supporting the patient, researchers, administrators, payors, and supportive associates of the given patient.

10. A methodology as in claim 9, further including subsequently interactively conducting the same or a different survey for the given patient at a later point in time, and reporting an updated relative score to at least one of the given patient, healthcare staff supporting the patient, researchers, administrators, payors, and supportive associates of the given patient.

11. A methodology as in claim 1, further including:
creating a database of measures of the patient's health status indicators and external social and economic variables to likelihood of adherence, to form a set of fact-based data for the given participant; and
collectively assessing the patient's internal self-reported data and fact-based data to determine a relative score for the given patient for likelihood to adhere to a healthcare treatment plan for the given patient.

12. A methodology as in claim 11, wherein the patient's health status indicators include at least one of body mass index (BMI), blood A1c levels, and Rx fill/refill data for the given patient.

13. A methodology as in claim 1, wherein the healthcare treatment plan comprises at least one of a plan of treatment for a particular condition of a given patient and a wellness activities plan for a given patient.

14. A methodology as in claim 1, wherein the items include at least one of a question, an image, a statement, a sound bite, and a video file presented to the patient for capture of the patient's subjective response thereto.

15. A methodology for predictively determining a participant's likelihood to adhere to an activity plan for such participant, comprising:
   interactively conducting a survey for a given participant by having the participant use a movable feature of a graphical interface on a display to respectively capture and definitively measure through non-verbal communication the participant's self-reported internal subjective feelings in response to a plurality of survey items concerning affect-based variables to likelihood of adherence, to form a set of internal self-reported data for the given participant, wherein the graphical interface comprises digital graphic shape-shifting icons for such participant to view on said display, with the participant using the movable feature to manipulate the appearance of each respective icon through a range of appearances thereof so that it reflects the self-reported intensity of how such participant subjectively feels in response to each item of the participant survey;
   creating a database of measures of the participant's external social and economic variables to likelihood of adherence, to form a set of external fact-based data for the given participant; and
   collectively assessing the participant's internal self-reported data and external fact-based data to determine a relative score for such participant for likelihood to adhere to an activity plan.

16. A methodology as in claim 15, wherein:
   said affect-based variables comprise determined obstacles to achievement of activities in an activity plan.

17. A methodology as in claim 16, wherein said digital graphic displays comprise a plurality of shape-shifting icons with at least one icon for each respective survey item and a movable element for the participant to manipulate a shape-shifting icon through a range of appearances designed to correlate with the intensity of the participant's feelings in response to a survey item, with the appearances of the shape-shifting icons pre-validated for a population of participants in which the given participant is a member, to validate that each icon represents the subject matter of its associated item and attendant range of intensities thereof.

18. A methodology as in claim 15, wherein collectively assessing the participant's internal self-reported data and external fact-based data includes establishing one of a relatively high, medium, or low probability for such participant for likelihood to adhere to an activity plan.

19. A methodology as in claim 15, wherein collectively assessing the participant's internal self-reported data and external fact-based data includes establishing a specific score within an indexed range to relatively assess the probability for such participant for likelihood to adhere to an activity plan.

20. A methodology as in claim 19, wherein the indexed range comprises a scaled range from between 0 and 100.

21. A methodology as in claim 15, wherein the participant comprises a potential consumer for a given product, and the survey items relate to a particular product or service of potential interest to the potential consumer, as part of evaluating customer experiences or conducting consumer research relative to such particular product or service.

22. A methodology as in claim 16, wherein the participant comprises a patient and the activity plan comprises a health treatment plan for the patient.

23. A methodology as in claim 22, further including subsequently interactively conducting the same or a different survey for the given patient at a later point in time, and reporting an updated relative score to at least one of the given patient, healthcare staff supporting the patient, researchers, administrators, payors, and supportive associates of the given patient.

24. A methodology as in claim 22, wherein the external social and economic variables to likelihood of adherence for a patient comprise social/economic factors experienced by an individual patient that negatively impact medical treatment plan adherence, including at least one of low socioeconomic status, low health literacy, low levels of education, low levels of social support, unemployment, housing instability, family dysfunction, barriers with transportation to medical care, high medication costs, and negative cultural beliefs about medical treatment.

25. A methodology as in claim 16, wherein the internal subjective feelings which are variables to likelihood of adherence for a patient include self-reported felt sense and intensity thereof for at least one of wellness versus illness, stress, depression, anxiety, pain, and loneliness of the patient.

26. A methodology as in claim 25, wherein the internal subjective feelings further include a patient's self-reported sense and intensity of satisfaction with the patient's most recent health provider/staff interaction.

27. A methodology as in claim 15, wherein the survey items include at least one of a question, an image, a statement, a sound bite, and a video file presented to the participant for capture of the participant's subjective response thereto.

28. A system for predictively determining a given patient's likelihood to adhere to a healthcare treatment plan for such patient, comprising:
   a memory;
   a display; and
   a processor coupled to the memory programmed with executable instructions, the instructions including:
   a patient survey comprising a plurality of survey items to be administered to a given patient and related to selected determined obstacles to adherence to a healthcare treatment plan for such patient,
   a patient graphical interface comprising digital graphic shape-shifting icons for such patient to view on said display, and to capture and definitively measure through non-verbal communication subjective experiences thereof by such patient by having such patient use a movable feature to manipulate the appearance of each respective icon through a range of appearances thereof so that it reflects the self-reported intensity of how such patient subjectively feels in response to each item of the patient survey, and an assessing component, for assessing such patient's set of self-reported responses to determine a relative score for such patient for likelihood to adhere to a healthcare treatment plan.

29. A system as in claim 28, wherein the system is implemented via a hardware and software platform comprising a plurality of network-based non-transitory storage devices, servers, and processors, which are accessible by authorized users.

30. A system as in claim 29, wherein the system includes at least one network-based non-transitory storage device for being accessed by authorized users, for the update and storage therein of data on at least one particular patient concerning at least one of background external health, social, and economic variables to likelihood of adherence for such particular patient.

31. A system as in claim 29, wherein the system includes at least one network-based non-transitory storage device for being accessed by at least one particular patient, for the update and storage therein of data on at least one of definitively measured subjective experiences for such particular patient in response to at least one item of the patient survey.

32. A system as in claim 30, wherein:
the system includes at least one network-based non-transitory storage device for being accessed by at least one particular patient, for the update and storage therein of data on at least one of definitively measured subjective experiences for such particular patient in response to at least one item of the patient survey; and
the assessing component is further operative for collectively assessing such patient's set of responses along with stored data on such patient concerning background external health, social, and economic variables to likelihood of adherence, to determine a relative score for such patient for likelihood to adhere to a healthcare treatment plan.

33. A system as in claim 32, wherein the assessing component is further operative for collectively assessing such patient's set of self-reported responses normalized relative to stored data of anonymized results from a plurality of other patients with common or similar background data.

34. A system as in claim 32, wherein the assessing component is further operative for storing on at least one network-based non-transitory storage device the self-reported responses and relative score for such patient for likelihood to adhere to a healthcare treatment plan, to be accessed by authorized users.

35. A system as in claim 34, wherein the assessing component is further operative for storing on such at least one network-based non-transitory storage device the self-reported responses and relative scores for such patient, based on repeated administrations of the same or a different patient survey to such patient, for likelihood to adhere to a healthcare treatment plan data for such patient, to be accessed by authorized users.

36. A system as in claim 32, wherein the system further includes a reporting device for preparing a report of data otherwise stored on at least one network-based non-transitory storage device regarding the self-reported responses and relative score for such patient for likelihood to adhere to a healthcare treatment plan, and for transmitting the report to selected entities.

37. A system as in claim 36, wherein the selected entities comprise at least one of a given patient, healthcare staff supporting the given patient, researchers, administrators, payors, and supportive associates of the given patient.

38. A system as in claim 37, wherein the reporting device is operative for preparing a report covering time periods determined by the selected entity to receive the report.

39. A system as in claim 28, wherein the patient movable feature comprises a patient movable bar to manipulate at least one of each respective icon so that it reflects how the patient feels in response to each item.

40. A system as in claim 28, wherein the shape-shifting icons are pre-validated for a selected population of patients in which the given patient is a member, to validate that each icon and its range of appearances represents the subject matter of its associated item and attendant range of intensities thereof.

41. A system as in claim 40, wherein the shape-shifting icons are pre-validated through an iterative icon design process which focuses on a patient's perceived resonance between an icon and the corresponding subject matter being surveyed through use of such icon.

42. A system as in claim 41, wherein the iterative icon design process includes use of a forced-choice validation engine paradigm to study the correlation between an icon design and the subject matter to be surveyed through use of such icon.

43. A system as in claim 42, wherein the iterative icon design process further includes use of an intensity rating validation paradigm to study the correlation between an icon design and the range of intensities of a patient's feelings to be represented by such icon.

44. A system as in claim 28, wherein the healthcare treatment plan comprises at least one of a plan of treatment for a particular condition of a given patient and a wellness activities plan for a given patient.

45. A system as in claim 28, wherein the shape-shifting icons respectively comprise icons with changing aspects each including at least one of construction, display, and use including size, color, shape, opacity, and data input methods.

46. A system as in claim 28, wherein the patient graphical interface captures and definitively measures subjective experiences by rendering scaled values by having the patient use a movable bar to manipulate at least one of each respective icon so that it reflects how the patient feels in response to each item.

47. A system as in claim 28, wherein the relative score includes one of a relatively high, medium, or low likelihood to adhere to a healthcare treatment plan for such patient.

48. A system as in claim 28, wherein the relative score includes a specific score within an indexed range to relatively assess the likelihood to adhere to a healthcare treatment plan for such patient.

49. A system as in claim 48, wherein the indexed range comprises a scaled range from between 0 and 100.

50. A system as in claim 28, wherein the survey items include at least one of a question, an image, a statement, a sound bite, and a video file presented to the patient for capture of the patient's subjective response thereto.

51. A methodology as in claim 1, wherein assessing the patient's set of data includes establishing a specific score within an indexed range to relatively assess the probability of adherence to a healthcare treatment plan and cohorts for the given patient.

52. A methodology as in claim 51, wherein the indexed range comprises a scaled and normalized range from between 0 and a predetermined top scale number.

53. A methodology as in claim 52, wherein the predetermined top scale number falls into a range from 1 to 100.

54. A methodology as in claim 22, wherein creating a database of measures further includes creating a database of measures of the participant's external social and economic variables, and external environment variables affecting a patient's likelihood of adherence, to form the set of external fact-based data for the given participant.

55. A methodology as in claim 54, wherein the external social and economic variables and external variables to likelihood of adherence for a patient comprise social/economic/environmental factors experienced by an individual patient that negatively impact medical treatment plan adherence, including at least one of low socioeconomic status, low health literacy, low levels of education, low levels of social support, unemployment, housing instability, poor environmental conditions, family dysfunction, barriers with transportation to medical care, high medication costs, and negative cultural beliefs about medical treatment.

56. A methodology as in claim 19, wherein the indexed range comprises a scaled and normalized range from between 0 and a predetermined top scale number.

57. A methodology as in claim 56, wherein the predetermined top scale number falls into a range from 1 to 100.

58. A system as in claim 48, wherein the indexed range comprises a scaled and normalized range from between 0 and a predetermined top scale number.

59. A system as in claim 58, wherein the predetermined top scale number falls into a range from 1 to 100.

\* \* \* \* \*